United States Patent
Semenov

(10) Patent No.: US 9,072,449 B2
(45) Date of Patent: Jul. 7, 2015

(54) WEARABLE/MAN-PORTABLE ELECTROMAGNETIC TOMOGRAPHIC IMAGING

(71) Applicant: EMTensor GmbH, Vienna (AT)

(72) Inventor: Serguei Y Semenov, Vienna (AT)

(73) Assignee: EMTensor GmbH, Vienna (AT)

( * ) Notice: Subject to any disclaimer, the term of this patent is extended or adjusted under 35 U.S.C. 154(b) by 213 days.

(21) Appl. No.: 13/894,395

(22) Filed: May 14, 2013

(65) Prior Publication Data

US 2014/0276012 A1      Sep. 18, 2014

Related U.S. Application Data

(60) Provisional application No. 61/801,965, filed on Mar. 15, 2013.

(51) Int. Cl.
| | |
|---|---|
| *A61B 6/02* | (2006.01) |
| *A61B 5/05* | (2006.01) |
| *A61B 6/00* | (2006.01) |
| *A61B 5/00* | (2006.01) |

(52) U.S. Cl.
CPC ............... *A61B 5/0507* (2013.01); *A61B 6/542* (2013.01); *A61B 2562/143* (2013.01); *A61B 2562/0228* (2013.01); *A61B 5/0042* (2013.01); *A61B 5/4312* (2013.01)

(58) Field of Classification Search
CPC ........... A61B 5/0507; A61B 2562/143; A61B 2562/0228; A61B 6/542; A61B 5/0042; A61B 5/4312
See application file for complete search history.

(56) References Cited

U.S. PATENT DOCUMENTS

| | | |
|---|---|---|
| 4,135,131 A | 1/1979 | Larsen et al. |
| 4,157,472 A | 6/1979 | Beck, Jr. et al. |
| 4,247,815 A | 1/1981 | Larsen et al. |
| 4,638,813 A | 1/1987 | Turner |

(Continued)

FOREIGN PATENT DOCUMENTS

| | | |
|---|---|---|
| EP | 2404550 A1 | 1/2012 |
| RU | 2011128101 A | 1/2013 |

(Continued)

OTHER PUBLICATIONS

Information Disclosure Statement (IDS) Letter Regarding Common Patent Application(s), dated Aug. 12, 2014.

(Continued)

*Primary Examiner* — Long V Le
*Assistant Examiner* — Angela M Hoffa
(74) *Attorney, Agent, or Firm* — Tillman Wright, PLLC; James D. Wright; David R. Higgins

(57) ABSTRACT

A system for wearable/man-portable electromagnetic tomographic imaging includes a wearable/man-portable boundary apparatus adapted to receive a biological object within, a position determination system, electromagnetic transmitting/receiving hardware, and a hub computer system. The electromagnetic transmitting/receiving hardware collectively generates an electromagnetic field that passes into the boundary apparatus and receives the electromagnetic field after being scattered/interferenced by the biological object within. The hub computer system performs electromagnetic tomographic imaging based on the received electromagnetic field.

30 Claims, 16 Drawing Sheets

(56) References Cited

U.S. PATENT DOCUMENTS

| | | | |
|---|---|---|---|
| 4,662,222 | A | 5/1987 | Johnson |
| 4,798,209 | A | 1/1989 | Klingenbeck et al. |
| 4,805,627 | A | 2/1989 | Klingenbeck et al. |
| 4,926,868 | A | 5/1990 | Larsen |
| 5,069,223 | A | 12/1991 | McRae |
| 5,222,501 | A | 6/1993 | Ideker et al. |
| 5,233,713 | A | 8/1993 | Murphy et al. |
| 5,263,050 | A | 11/1993 | Sutterlin et al. |
| 5,305,748 | A | 4/1994 | Wilk |
| 5,363,050 | A | 11/1994 | Guo et al. |
| 5,405,346 | A | 4/1995 | Grundy et al. |
| 5,715,819 | A | 2/1998 | Svenson et al. |
| 6,026,173 | A | 2/2000 | Svenson et al. |
| 6,073,047 | A | 6/2000 | Barsamian et al. |
| 6,332,087 | B1 | 12/2001 | Svenson et al. |
| 6,333,087 | B1 | 12/2001 | Jerdee et al. |
| 6,490,471 | B2 | 12/2002 | Svenson et al. |
| 6,522,910 | B1 | 2/2003 | Gregory |
| 6,697,660 | B1 | 2/2004 | Robinson |
| 6,865,494 | B2 | 3/2005 | Duensing et al. |
| 7,239,731 | B1 | 7/2007 | Semenov et al. |
| 7,272,431 | B2 | 9/2007 | McGrath |
| 7,340,292 | B2 | 3/2008 | Li |
| 7,876,114 | B2 | 1/2011 | Campbell et al. |
| 8,000,775 | B2 | 8/2011 | Pogue et al. |
| 8,089,417 | B2 | 1/2012 | Popovic et al. |
| 8,207,733 | B2 | 6/2012 | Meaney et al. |
| 8,253,619 | B2 | 8/2012 | Holbrook et al. |
| 8,376,948 | B2 | 2/2013 | Brannan |
| 8,724,864 | B2 | 5/2014 | Persson et al. |
| 2002/0168317 | A1 | 11/2002 | Daighighian et al. |
| 2003/0088180 | A1 | 5/2003 | Van Veen et al. |
| 2003/0090276 | A1 | 5/2003 | Weide et al. |
| 2004/0123667 | A1* | 7/2004 | McGrath ............ 73/704 |
| 2006/0133564 | A1 | 6/2006 | Langan et al. |
| 2007/0238957 | A1 | 10/2007 | Yared |
| 2008/0319437 | A1 | 12/2008 | Turner et al. |
| 2010/0010340 | A1 | 1/2010 | Godavarty et al. |
| 2010/0067770 | A1 | 3/2010 | Persson et al. |
| 2010/0174179 | A1 | 7/2010 | Persson et al. |
| 2011/0022325 | A1 | 1/2011 | Craddock et al. |
| 2011/0263961 | A1 | 10/2011 | Craddock et al. |
| 2011/0295102 | A1 | 12/2011 | Lakkis et al. |
| 2012/0010493 | A1 | 1/2012 | Semenov |
| 2012/0083683 | A1 | 4/2012 | Kuwabara |
| 2012/0083690 | A1 | 4/2012 | Semenov |
| 2012/0172954 | A1 | 7/2012 | Zastrow et al. |
| 2012/0179037 | A1 | 7/2012 | Halmann |
| 2012/0190977 | A1 | 7/2012 | Persson et al. |
| 2014/0024917 | A1* | 1/2014 | McMahon et al. ............ 600/407 |
| 2014/0155740 | A1 | 6/2014 | Semenov |
| 2014/0275944 | A1* | 9/2014 | Semenov ............ 600/407 |
| 2014/0378812 | A1* | 12/2014 | Saroka et al. ............ 600/407 |

FOREIGN PATENT DOCUMENTS

| | | |
|---|---|---|
| WO | 9532665 | 12/1995 |
| WO | 2007136334 A1 | 11/2007 |
| WO | 2008002251 A1 | 1/2008 |
| WO | 2011009945 A2 | 1/2011 |
| WO | 2011156810 A2 | 12/2011 |
| WO | 2013005134 A2 | 1/2013 |
| WO | 2014081992 A2 | 5/2014 |
| WO | 2014150616 A2 | 9/2014 |
| WO | 2014150618 A1 | 9/2014 |
| WO | 2014150616 A3 | 12/2014 |

OTHER PUBLICATIONS

"International Search Report" and "Written Opinion of the International Searching Authority" (ISA/US) in EMTensor GmbH, International Patent Application Serial No. PCT/US2013/071360, mailed May 27, 2014 (20 pages).

"International Search Report" and "Written Opinion of the International Searching Authority" (ISA/US) in EMTensor GmbH, International Patent Application Serial No. PCT/US2014/023803, mailed Jun. 25, 2014 (9 pages).

"European Search Report" and "Written Opinion of the European Patent Office" in European Patent Application No. 11275103.7 for EMImaging Limited, dated Oct. 13, 2011, 5 pages.

Serguei Semenov: "Microwave tomography: review of the progress towards clinical applications", Philosophical Transactions of the Royal Society, vol. 2009, No. 367, Dec. 31, 2009. [pp. 3021-3042, XP002661164. DOI: 10.1098/rsta.2009.0092 *The whole document*.

Semenov S Y et al: "Development of microwave tomography for functional cardiac imaging", Biomedical Imaging: Macro to Nano, 2004, Piscataway, NJ, USA, IEEE, Apr. 15, 2004, pp. 1351-1353, XP010774114, DOI: 10.1109/ISB1.2004.1398797 ISBN: 978-0/7803-8389-0 *the whole document*.

Information Disclosure Statement (IDS) Letter Regarding Common Patent Application(s), dated Dec. 5, 2013.

Information Disclosure Statement (IDS) Letter Regarding Common Patent Application(s), dated Jan. 26, 2015.

Fear, Elise C., et al. "Confocal microwave imaging for breast cancer detection: Localization of tumors in three dimensions." IEEE Transactions of Biomedical Engineering 49.8 (2002): 812-822 (11 pages).

Yaniv, Ziv, et al. "Electromagnetic tracking in the clinical environment." Medical physics 36.3 (2009): 876-892 (17 pages).

"International Search Report" and "Written Opinion of the International Searching Authority" (ISA/US) in EMTensor GmbH, International Patent Application Serial No. PCT/US2014/023793, mailed Oct. 31, 2014 (11 pages).

* cited by examiner

WEARABLE/MAN-PORTABLE ELECTROMAGNETIC TOMOGRAPHIC IMAGING

CROSS-REFERENCE TO RELATED APPLICATION

The present application is a U.S. nonprovisional patent application of, and claims priority under 35 U.S.C. §119(e) to, U.S. provisional patent application Ser. No. 61/801,965, filed Mar. 15, 2013, which provisional patent application is incorporated by reference herein.

In addition, the entirety of U.S. Pat. No. 7,239,731 to Semenov et al., issued Jul. 3, 2007 and entitled "SYSTEM AND METHOD FOR NON-DESTRUCTIVE FUNCTIONAL IMAGING AND MAPPING OF ELECTRICAL EXCITATION OF BIOLOGICAL TISSUES USING ELECTROMAGNETIC FIELD TOMOGRAPHY AND SPECTROSCOPY," is incorporated herein by reference. The disclosure of this particular patent may provide background and technical information with regard to the systems and environments of the inventions described herein.

Also, the entirety of U.S. Patent Application Publication No. 2012/0010493 A1, which was published Jan. 12, 2012 based on U.S. patent application Ser. No. 13/173,078 to Semenov, filed Jun. 30, 2011 and entitled "SYSTEMS AND METHODS OF 4D ELECTROMAGNETIC TOMOGRAPHIC (EMT) DIFFERENTIAL (DYNAMIC) FUSED IMAGING," is incorporated herein by reference. The disclosure of this particular patent publication may provide explanation of the use of "4D" technology in EMT systems, including with regard to inventions described herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

1. Field of the Present Invention

The present invention relates generally to electromagnetic tomography, and, in particular but not exclusively, to electromagnetic tomographic imaging with man-portable components, including methods, devices, and systems.

2. Background

Electromagnetic tomography (EMT) is a relatively recent imaging modality with great potential for biomedical applications, including a non-invasive assessment of functional and pathological conditions of biological tissues. Using EMT, biological tissues are differentiated and, consequentially, can be imaged based on the differences in tissue dielectric properties. The dependence of tissue dielectric properties from its various functional and pathological conditions, such as blood and oxygen contents, ischemia and infarction malignancies has been demonstrated.

Two-dimensional (2D), three-dimensional (3D) and even "four-dimensional" (4D) EMT systems and methods of image reconstruction have been developed over the last decade or more. Feasibility of the technology for various biomedical applications has been demonstrated, for example, for cardiac imaging and extremities imaging.

As in any biomedical imaging, the classical EMT imaging scenario consists of cycles of measurements of complex signals, as scattered or "interferenced" by a biologic object under study, obtained from a plurality of transmitters located at various points around the object and measured on a plurality of receivers located at various points around the object. This is illustrated in FIG. 1. As recounted elsewhere herein, the measured matrix of scattered EM signals may then be used in image reconstruction methods in order to reconstruct a 2D or 3D distribution of dielectric properties of the object, i.e., to construct a 2D or 3D image of the object. Still further, 4D imaging may be achieved by reconstructing 3D images at different time points.

Generally, it is very important for image reconstruction to precisely describe a distribution of EM field with an imaging domain 21. The distribution of EM field with an imaging chamber is a very complex phenomenon, even when there is no object of interest inside.

FIG. 2 is a schematic view of one possible embodiment of a prior art EM field tomographic spectroscopic system 10. Such a system 10 could carry out functional imaging of biological tissues and could also be used for a non-invasive mapping of electrical excitation of biological tissues 19 using a sensitive (contrast) material (solution or nanoparticles) injected into the biological tissue 19 or in circulation system, characterized by having dielectric properties that are a function of electrical field, generated by biological excited tissue 19. As illustrated in FIG. 2, the system 10 included a working or imaging chamber 12, a plurality of "EM field source-detector" clusters 26, an equal number of intermediate frequency ("IF") detector clusters 28, and a control system (not shown). Although only two EM field source-detector clusters 26 and two IF detector clusters 28 are shown, a much larger number of each are actually used.

The imaging chamber 12 was a closed domain, such as a watertight vessel, of sufficient size to accommodate a human body or one or more parts of a human body. For example, the imaging chamber 12 may be a helmet-like imaging chamber to image brain disorders (for example acute and chronic stroke), ii) a cylindrical type chamber for extremities imaging, or iii) a specifically shaped imaging chamber for detection of breast cancer. As a result, the imaging chamber may have different shapes and sizes.

The imaging chamber 12 and its EM field clusters 26, as well as the IF detector clusters 28, have sometimes been mounted on carts in order to permit the respective components to be moved if necessary, and the carts may then be locked in place to provide stability.

Oversimplified, the system 10 operates as follows. An object of interest (e.g., biological tissue) is placed in the imaging domain 21. The transmitting hardware generates electromagnetic (EM) radiation and directs it to one of antennas. This antenna transmits electromagnetic waves into imaging domain 21, and all of the other antennas receive electromagnetic waves that have passed through some portion of the imaging domain 21. The receiving hardware detects the resulting signal(s), and then the same cycle is repeated for the next antenna and the next one until all antennas have served as a transmitter. As described, for example, in the aforementioned U.S. Pat. No. 7,239,731, code-division technology can be utilized such that the transmitting hardware generates EM radiation and directs it to a plurality of simultaneously transmitting antennas that are specifically coded by a unique "antenna specific code," so that the source of the resulting EM radiation received at a particular receiving antenna can be "recognized" on the basis of the codes. The end result is a matrix of complex data which is transmitted to one or more computers in the control system that process the data to produce an image of the object 19 in the imaging domain 21. An algorithm called an "inversion" algorithm is utilized in this process.

FIG. 4 is a schematic illustration of a three-dimensional setting for the system of FIG. 2.

Unfortunately, traditional EMT technologies, while producing very useful results, have required equipment that is physically cumbersome and difficult to use. This can be true both for the technician, diagnostician, or the like as well as the person or animal who is being studied. With regard to latter, the discomfort caused by the imaging chamber can also be significant. The size and weight of the equipment also makes it very difficult to use the equipment in the place where it is assembled; disassembling and moving the equipment is not very feasible. Finally, the use of arrays of antenna and other equipment creates significant complexity and cost. Thus, a need exists for technology that produces similar results but in a cheaper, more convenient, and more comfortable physical form.

Moreover, a need exists for the imaging and diagnostic capabilities offered by EMT technologies to be available in settings beyond the traditional clinic setting. In particular, a need exists for EMT technologies to be available in everyday human life, providing safe, on-demand, on-line (real time) screening and diagnosis.

SUMMARY OF THE PRESENT INVENTION

Broadly defined, the present invention according to one aspect is a system for wearable/man-portable electromagnetic tomographic imaging, including: a wearable/man-portable boundary apparatus adapted to receive a biological object within; a position determination system; electromagnetic transmitting/receiving hardware that collectively generates an electromagnetic field that passes into the boundary apparatus and receives the electromagnetic field after being scattered/interferenced by the biological object within; and a hub computer system for performing electromagnetic tomographic imaging based upon the generated and received electromagnetic field and upon position information from the position determination system.

In a feature of this aspect, the wearable/man-portable boundary apparatus is a hollow structure whose walls include a plurality of electromagnetic windows through which the electromagnetic field enters and leaves.

In a further feature of this aspect, the walls of the hollow structure define the boundaries of an imaging domain and are made at least partly of a material that is non-transparent with respect to the electromagnetic field generated by the electromagnetic transmitting/receiving hardware, and wherein the plurality of electromagnetic windows are distributed in the walls so as to surround the imaging domain.

In another further feature of this aspect, the plurality of electromagnetic windows have known spatial locations. In further features, each electromagnetic window may be independently opened and closed to control whether the electromagnetic field enters and/or leaves therethrough; each electromagnetic window may be independently opened and closed via a respective microgate; the microgates are controlled such that the electromagnetic field enters into the boundary apparatus through only one electromagnetic window at a time; the microgates are controlled such that the electromagnetic field enters into the boundary apparatus through a plurality of electromagnetic windows at a time; the microgates are controlled such that the electromagnetic field leaves the boundary apparatus through only one electromagnetic window at a time; the microgates are controlled such that the electromagnetic field leaves the boundary apparatus through a plurality of electromagnetic windows at a time; each microgate is individually coded; and/or as the electromagnetic field enters the boundary apparatus through an open electromagnetic window, the coding of the microgate for the open electromagnetic window is applied to the electromagnetic field. Knowledge of the spatial locations of the plurality of electromagnetic windows may be determined via the position determination system; and/or knowledge of the spatial locations of the plurality of electromagnetic windows may be established independently of the position determination system.

In another further feature of this aspect, the position determination system determines information about the position of the boundary apparatus, and the hub computer system performs magnetic tomographic imaging based upon the received electromagnetic field and upon the boundary apparatus position information from the position determination system.

In another further feature of this aspect, the position determination system determines information about the positions of the electromagnetic windows, and the hub computer system performs magnetic tomographic imaging based upon the received electromagnetic field and upon the electromagnetic windows position information from the position determination system.

In another further feature of this aspect, the position determination system includes a first position determination system that determines information about the position of the boundary apparatus, the position determination system includes a second position determination system that determines information about the positions of the electromagnetic windows, and the hub computer system performs magnetic tomographic imaging based upon the received electromagnetic field and upon the boundary apparatus position information and electromagnetic windows position information from the position determination system.

In another further feature of this aspect, the boundary apparatus is in the form of a wearable hat.

In another further feature of this aspect, the boundary apparatus is in the form of a wearable shirt.

In another further feature of this aspect, the boundary apparatus is in the form of a wearable vest.

In another further feature of this aspect, the boundary apparatus is in the form of a wearable sleeve.

In another further feature of this aspect, the boundary apparatus is in the form of a wearable undergarment. In a further feature, the wearable undergarment is a wearable bra.

In another feature of this aspect, the electromagnetic transmitting/receiving hardware is man-portable.

In another feature of this aspect, the electromagnetic transmitting/receiving hardware is a small cellular base station.

In another feature of this aspect, the electromagnetic transmitting/receiving hardware includes transmitting hardware that is man-portable.

In another feature of this aspect, the electromagnetic transmitting/receiving hardware includes receiving hardware that is man-portable.

In another feature of this aspect, the electromagnetic transmitting/receiving hardware is physically separate from the boundary apparatus.

Broadly defined, the present invention according to another aspect is a wearable boundary apparatus, for use in electromagnetic tomographic imaging, including: a hollow structure having walls defining the boundaries of an imaging domain and made at least partially of a material that is non-transparent with respect to an electromagnetic field generated by separate electromagnetic transmitting/receiving hardware; a plurality of electromagnetic windows distributed in the walls so as to surround the imaging domain; and a plurality microgates that open and close the electromagnetic windows so as to control whether the electromagnetic field enters and/or leaves therethrough.

In a feature of this aspect, the wearable boundary apparatus is adapted to receive a biological object therein for a purpose of performing electromagnetic tomographic imaging on the object via the electromagnetic windows and the microgates.

In a further feature of this aspect, the plurality of electromagnetic windows have known spatial locations. In further features, each electromagnetic window may be independently opened and closed to control whether the electromagnetic field enters and/or leaves therethrough; each electromagnetic window may be independently opened and closed via a respective microgate; the microgates may be controlled such that the electromagnetic field enters into the boundary apparatus through only one electromagnetic window at a time; the microgates may be controlled such that the electromagnetic field enters into the boundary apparatus through a plurality of electromagnetic windows at a time; the microgates may be controlled such that the electromagnetic field leaves the boundary apparatus through only one electromagnetic window at a time; the microgates may be controlled such that the electromagnetic field leaves the boundary apparatus through a plurality of electromagnetic windows at a time; each microgate is individually coded; and/or as the electromagnetic field enters the boundary apparatus through an open electromagnetic window, the coding of the microgate for the open electromagnetic window is applied to the electromagnetic field.

In another further feature of this aspect, the boundary apparatus is in the form of a wearable hat.

In another further feature of this aspect, the boundary apparatus is in the form of a wearable shirt.

In another further feature of this aspect, the boundary apparatus is in the form of a wearable vest.

In another further feature of this aspect, the boundary apparatus is in the form of a wearable sleeve.

In another further feature of this aspect, the boundary apparatus is in the form of a wearable undergarment. In a further feature, the wearable undergarment is a wearable bra.

Broadly defined, the present invention according to another aspect is a method of electromagnetic tomographically imaging a live human body part using a wearable boundary apparatus, including: installing a wearable and portable boundary apparatus such that it is worn around a body part by a live human while the human moves from once place to another; determining position information pertaining to the wearable boundary apparatus; generating an electromagnetic field that passes into and out of the wearable boundary apparatus; receiving the electromagnetic field after being scattered/interferenced by the live human body part; and performing electromagnetic tomographic imaging based upon the generated and received electromagnetic field and upon the determined position information.

In a feature of this aspect, the step of installing a wearable and portable boundary apparatus includes installing a wearable and portable boundary apparatus that is a hollow structure whose walls include a plurality of electromagnetic windows through which the electromagnetic field passes in the generating step.

In a further feature of this aspect, the walls of the hollow structure define the boundaries of an imaging domain and are made at least partly of a material that is non-transparent with respect to the electromagnetic field generated by the electromagnetic transmitting/receiving hardware, and wherein the plurality of electromagnetic windows are distributed in the walls so as to surround the imaging domain.

In another further feature of this aspect, the method further includes a step of incorporating information about the spatial location of each of the plurality of electromagnetic windows. In further features, the method further includes a step of independently opening or closing the electromagnetic windows to control whether the electromagnetic field passes therethrough; the step of independently opening or closing the electromagnetic windows is carried out via a respective microgate for each electromagnetic window; the step of independently opening or closing the electromagnetic windows includes controlling the microgates such that the electromagnetic field passes into the boundary apparatus through only one electromagnetic window at a time; the step of independently opening or closing the electromagnetic windows includes controlling the microgates such that the electromagnetic field passes into the boundary apparatus through a plurality of electromagnetic windows at a time; the step of independently opening or closing the electromagnetic windows includes controlling the microgates such that the electromagnetic field passes out of the boundary apparatus through only one electromagnetic window at a time; the step of independently opening or closing the electromagnetic windows includes controlling the microgates such that the electromagnetic field passes out of the boundary apparatus through a plurality of electromagnetic windows at a time; each microgate is individually coded; the method further includes a step, as the electromagnetic field enters the boundary apparatus through an open electromagnetic window, of applying the coding of the microgate for the open electromagnetic window to the electromagnetic field; the method further includes a step of determining, via the position determination system, the information incorporated about the spatial location of each of the plurality of electromagnetic windows; and/or the method further includes a step of establishing, independently of the position determination system, the information incorporated about the spatial location of each of the plurality of electromagnetic windows.

In another further feature of this aspect, the method further includes a step of determining, via the position determination system, information about the position of the boundary apparatus, and wherein the step of performing electromagnetic tomographic imaging is performed by a hub computer system based upon the received electromagnetic field and upon the boundary apparatus position information from the position determination system.

In another further feature of this aspect, the method further includes a step of determining, via the position determination system, information about the positions of the electromagnetic windows, and wherein the step of performing electromagnetic tomographic imaging is performed by a hub computer system based upon the received electromagnetic field and upon the electromagnetic windows position information from the position determination system.

In another further feature of this aspect, the step of determining position information pertaining to the wearable boundary apparatus includes determining information, via a first position determination system, about the position of the boundary apparatus, the step of determining position information pertaining to the wearable boundary apparatus further includes determining information, via a second position determination system, about the positions of the electromagnetic windows, and the step of performing electromagnetic tomographic imaging is performed by a hub computer system based upon the received electromagnetic field and upon the boundary apparatus position information and electromagnetic windows position information from the position determination system.

In another further feature of this aspect, the boundary apparatus is in the form of a wearable hat, and wherein the step of installing a wearable and portable boundary apparatus includes wearing the hat on the head of the live human.

In another further feature of this aspect, the boundary apparatus is in the form of a wearable shirt, and wherein the step of installing a wearable and portable boundary apparatus includes wearing the shirt on the torso of the live human.

In another further feature of this aspect, the boundary apparatus is in the form of a wearable vest, and wherein the step of installing a wearable and portable boundary apparatus includes wearing the vest on the torso of the live human.

In another further feature of this aspect, the boundary apparatus is in the form of a wearable sleeve, and wherein the step of installing a wearable and portable boundary apparatus includes wearing the shirt on an arm of the live human.

In another further feature of this aspect, the boundary apparatus is in the form of a wearable undergarment. In a further feature, the wearable undergarment is a wearable bra, and wherein the step of installing a wearable and portable boundary apparatus includes wearing the bra around the breasts of the live human.

In another feature of this aspect, the steps of generating and receiving the electromagnetic field are carried out by electromagnetic transmitting/receiving hardware, and wherein the electromagnetic transmitting/receiving hardware is man-portable.

In another feature of this aspect, the steps of generating and receiving the electromagnetic field are carried out by electromagnetic transmitting/receiving hardware, and wherein the electromagnetic transmitting/receiving hardware is a small cellular base station.

In another feature of this aspect, the steps of generating and receiving the electromagnetic field are carried out by electromagnetic transmitting/receiving hardware, and wherein the electromagnetic transmitting/receiving hardware includes transmitting hardware that is man-portable.

In another feature of this aspect, the steps of generating and receiving the electromagnetic field are carried out by electromagnetic transmitting/receiving hardware, and wherein the electromagnetic transmitting/receiving hardware includes receiving hardware that is man-portable.

In another feature of this aspect, the steps of generating and receiving the electromagnetic field are carried out by electromagnetic transmitting/receiving hardware, and wherein the electromagnetic transmitting/receiving hardware is physically separate from the boundary apparatus.

In another feature of this aspect, the step of performing electromagnetic tomographic imaging is carried out by a hub computer system.

Broadly defined, the present invention according to another aspect is a method of electromagnetic tomographically imaging a biological object using a boundary apparatus, including: providing a boundary apparatus comprising a hollow structure, wherein the hollow structure includes walls defining the boundaries of an imaging domain, is made at least partially of a material that is non-transparent with respect to an electromagnetic field generated by electromagnetic transmitting/receiving hardware, and has a plurality of electromagnetic windows distributed in the walls so as to surround the imaging domain; opening one or more of the plurality of electromagnetic windows so as to control whether an electromagnetic field can enter and/or leave therethrough; generating an electromagnetic field that passes into the wearable boundary apparatus through the opened electromagnetic windows; receiving the electromagnetic field after being scattered/interferenced by the biological object; and performing electromagnetic tomographic imaging based upon the generated and received electromagnetic field.

In a feature of this aspect, the wearable boundary apparatus is adapted to receive a biological object therein for a purpose of performing the electromagnetic tomographic imaging step.

In a further feature of this aspect, the method further includes a step of incorporating information about the spatial location of each of the plurality of electromagnetic windows. In further features, the method further includes a step of independently opening or closing the electromagnetic windows to control whether the electromagnetic field passes therethrough; the step of independently opening or closing the electromagnetic windows includes controlling the microgates such that the electromagnetic field enters into the boundary apparatus through only one electromagnetic window at a time; the step of independently opening or closing the electromagnetic windows includes controlling the microgates such that the electromagnetic field enters into the boundary apparatus through only one electromagnetic window at a time; the step of independently opening or closing the electromagnetic windows includes controlling the microgates such that the electromagnetic field enters into the boundary apparatus through a plurality of electromagnetic windows at a time; the step of independently opening or closing the electromagnetic windows includes controlling the microgates such that the electromagnetic field passes out of the boundary apparatus through only one electromagnetic window at a time; the step of independently opening or closing the electromagnetic windows includes controlling the microgates such that the electromagnetic field passes out of the boundary apparatus through a plurality of electromagnetic windows at a time; each microgate is individually coded; and/or the method further includes a step, as the electromagnetic field enters the boundary apparatus through an open electromagnetic window, of applying the coding of the microgate for the open electromagnetic window to the electromagnetic field.

In another further feature of this aspect, the boundary apparatus is in the form of a wearable hat, and wherein the step of installing a wearable and portable boundary apparatus includes wearing the hat on the head of the live human.

In another further feature of this aspect, the boundary apparatus is in the form of a wearable shirt, and wherein the step of installing a wearable and portable boundary apparatus includes wearing the shirt on the torso of the live human.

In another further feature of this aspect, the boundary apparatus is in the form of a wearable vest, and wherein the step of installing a wearable and portable boundary apparatus includes wearing the vest on the torso of the live human.

In another further feature of this aspect, the boundary apparatus is in the form of a wearable sleeve, and wherein the step of installing a wearable and portable boundary apparatus includes wearing the shirt on an arm of the live human.

In another further feature of this aspect, the boundary apparatus is in the form of a wearable undergarment. In a further feature, the wearable undergarment is a wearable bra, and wherein the step of installing a wearable and portable boundary apparatus includes wearing the bra around the breasts of the live human.

Broadly defined, the present invention according to another aspect is a system for wearable/man-portable electromagnetic tomographic imaging that includes a wearable/ man-portable boundary apparatus adapted to receive a biological object within, a position determination system, electromagnetic transmitting/receiving hardware, and a hub computer system. The electromagnetic transmitting/receiving hardware collectively generates an electromagnetic field that passes into the boundary apparatus and receives the electromagnetic field after being scattered/interferenced by the biological object within. The hub computer system for performs electromagnetic tomographic imaging based on the received electromagnetic field.

In features of this aspect, the wearable/man-portable boundary apparatus is a hollow structure whose walls include a plurality of electromagnetic holes through which the electromagnetic field enters and leaves; the plurality of electromagnetic holes have known spatial locations; and/or each electromagnetic hole may be independently opened and closed via a respective microgate.

In other features of this aspect, the microgates are controlled such that the electromagnetic field enters passes into the boundary apparatus through only one electromagnetic hole at a time; each microgate is individually coded; the boundary apparatus is in the form of a wearable hat; the boundary apparatus is in the form of a wearable shirt; the boundary apparatus is in the form of a wearable vest; the boundary apparatus is in the form of a wearable sleeve; and/or the boundary apparatus is in the form of a wearable bra.

In still other features of this aspect, the electromagnetic transmitting/receiving hardware is man-portable; and/or the electromagnetic transmitting/receiving hardware is a small cellular base station.

Broadly defined, the present invention according to another aspect includes a system for wearable/man-portable electromagnetic tomographic imaging as shown and described.

Broadly defined, the present invention according to still another aspect includes a wearable boundary apparatus for use in electromagnetic tomographic imaging, as shown and described.

Broadly defined, the present invention according to still another aspect includes a method of wearable/man-portable electromagnetic tomographic imaging as shown and described.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
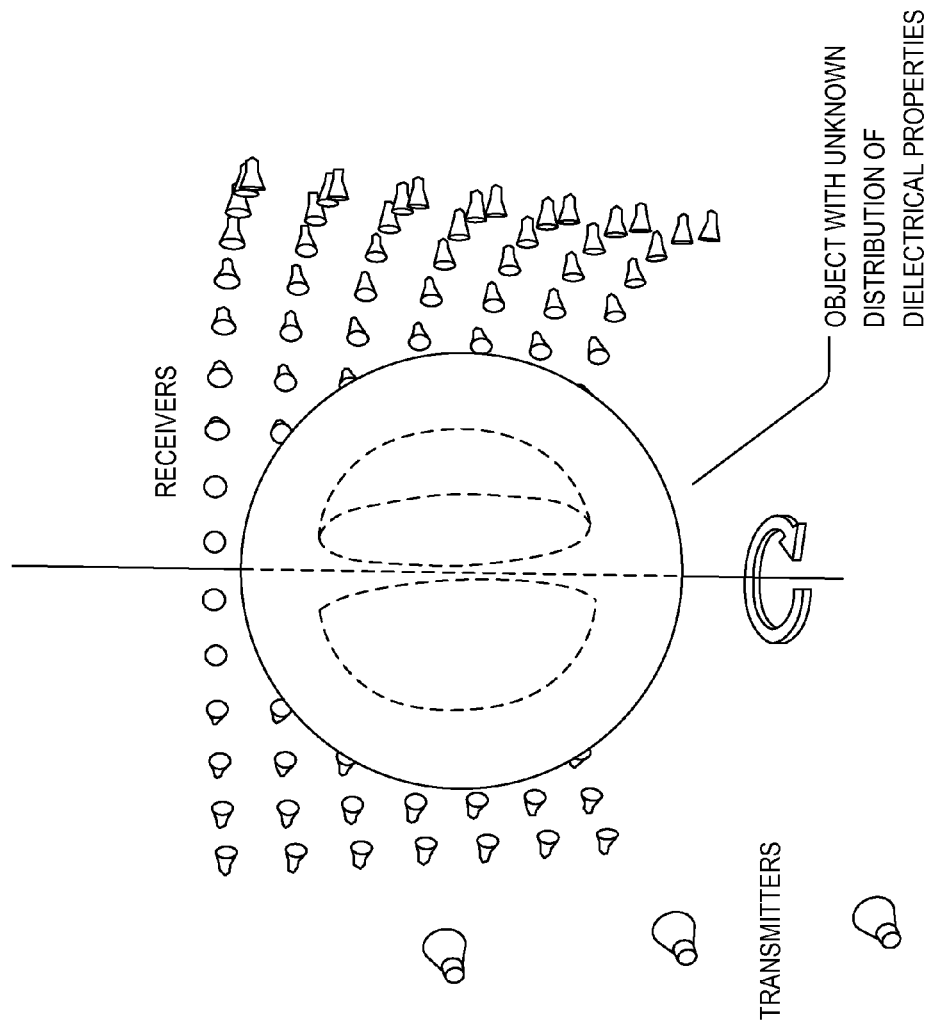
FIG. 1 is a graphical illustration of the principle of electromagnetic tomography (EMT)
Figure 2:
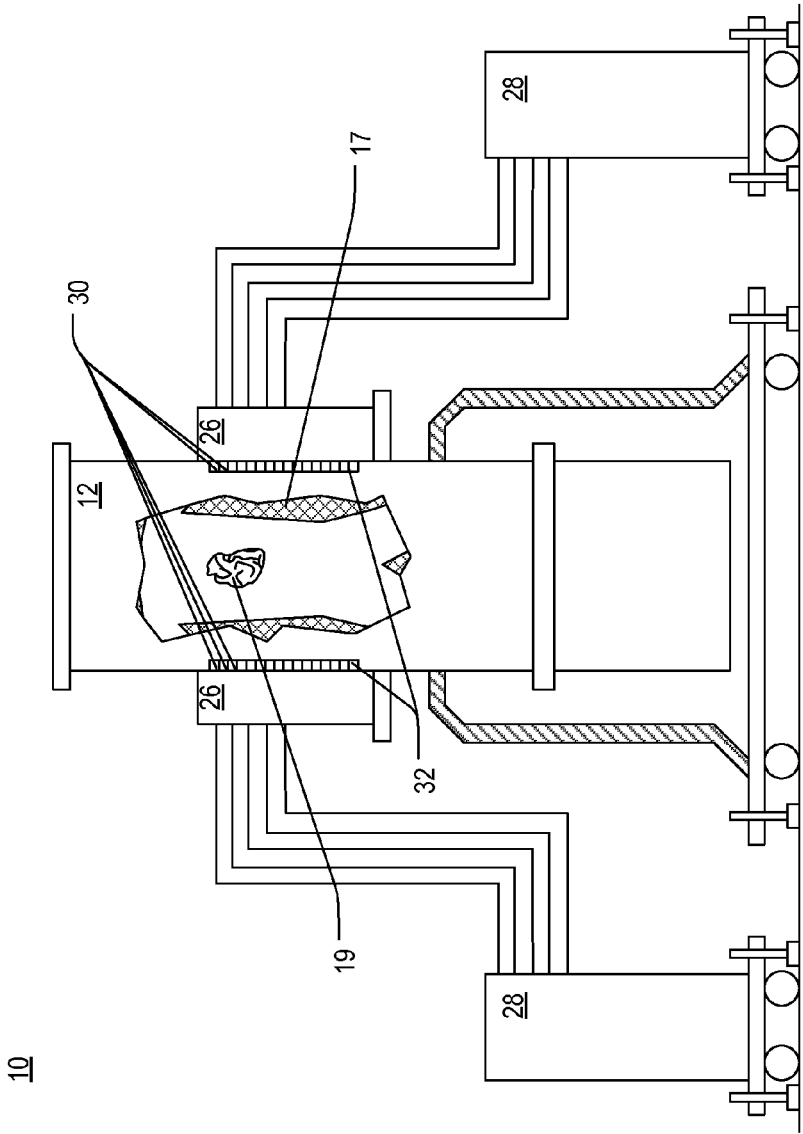
FIG. 2 is a schematic view of a prior art EM field tomographic spectroscopic system.
Figure 3:
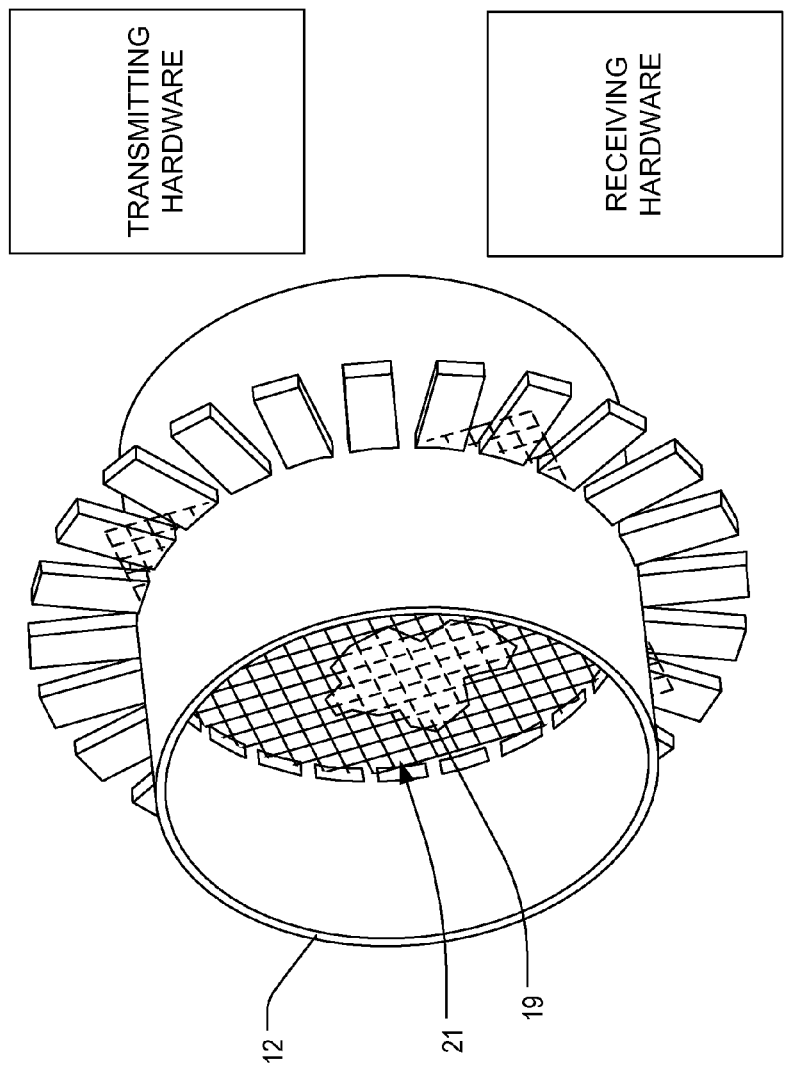
FIG. 3 is a schematic diagram illustrating the operation of the system of FIG. 1 in a two-dimensional context.
Figure 4:
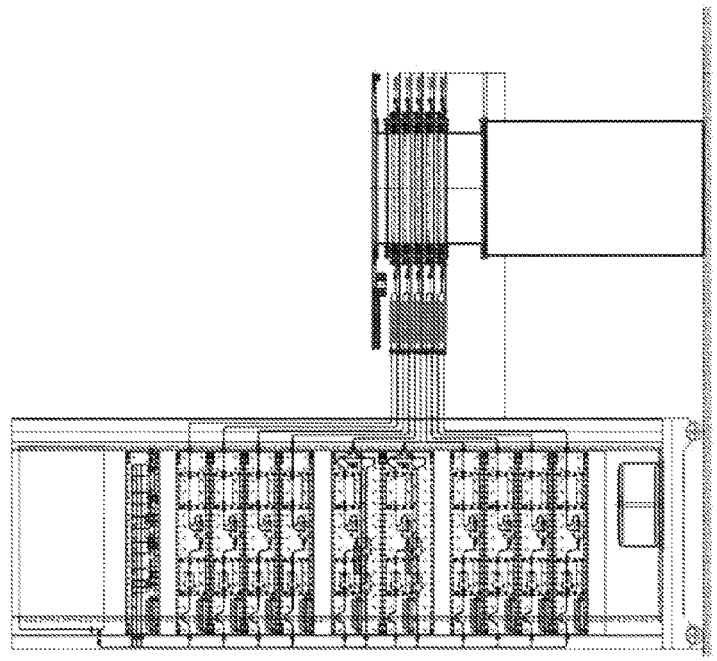
FIG. 4 is a schematic illustration of a three-dimensional setting for the system of FIG. 2.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers."Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, the preferred embodiments of the present invention are next described. The following description of one or more preferred embodiment(s) is merely exemplary in nature and is in no way intended to limit the invention, its application, or uses.

Figure 5:
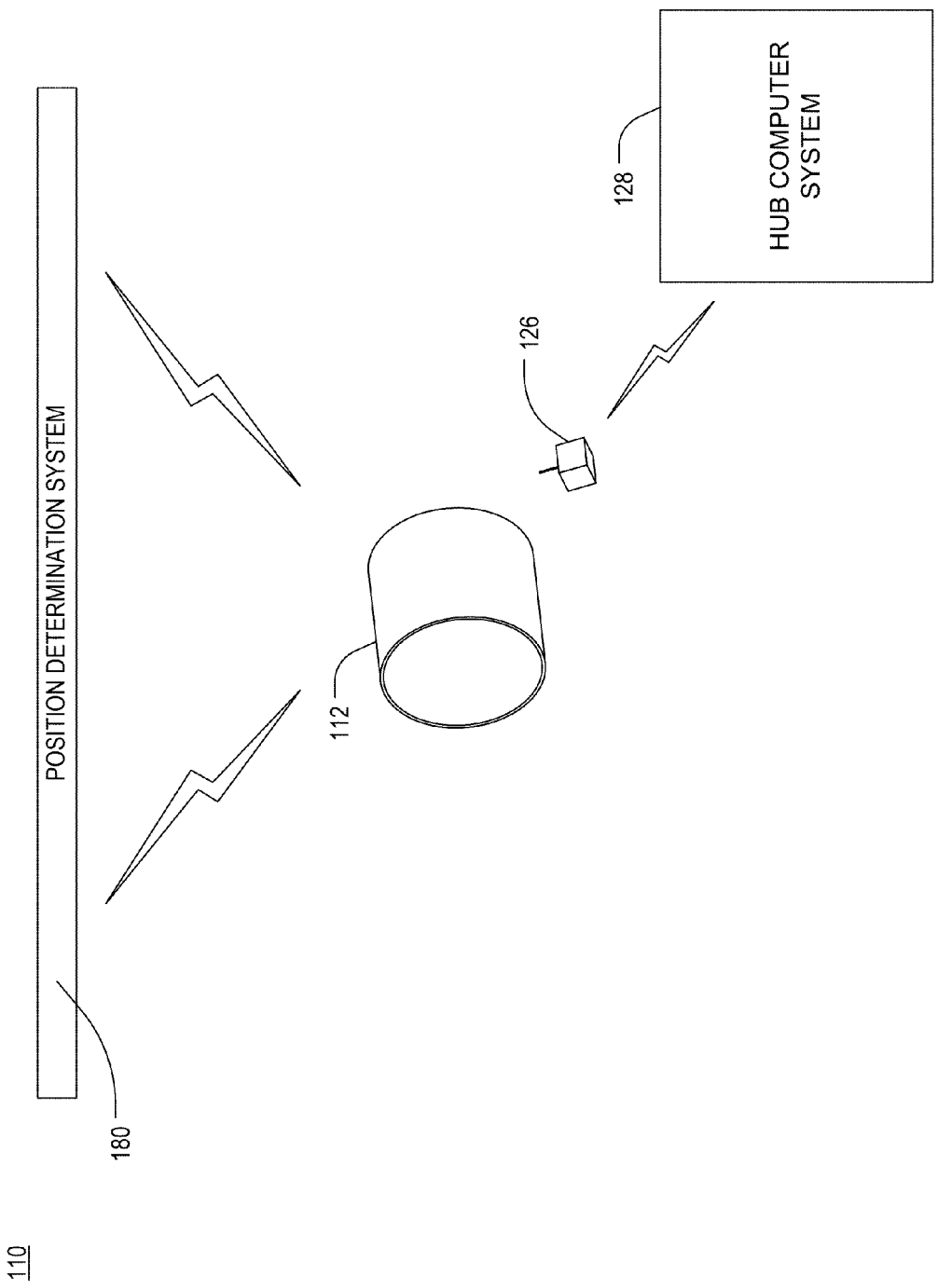
FIG. 5 is a block diagram of a system for wearable/man-portable electromagnetic tomographic imaging in accordance with a preferred embodiment of the present invention.

FIG. 5 is a block diagram of a system 110 for wearable/man-portable electromagnetic tomographic imaging in accordance with a preferred embodiment of the present invention. The system 110 includes a boundary apparatus 112, a position determination system 180, transmitting/receiving hardware 126, which includes a transmitter and a receiver, and a hub computer system 128. Each of these will be described in greater detail hereinbelow.

Figure 6:
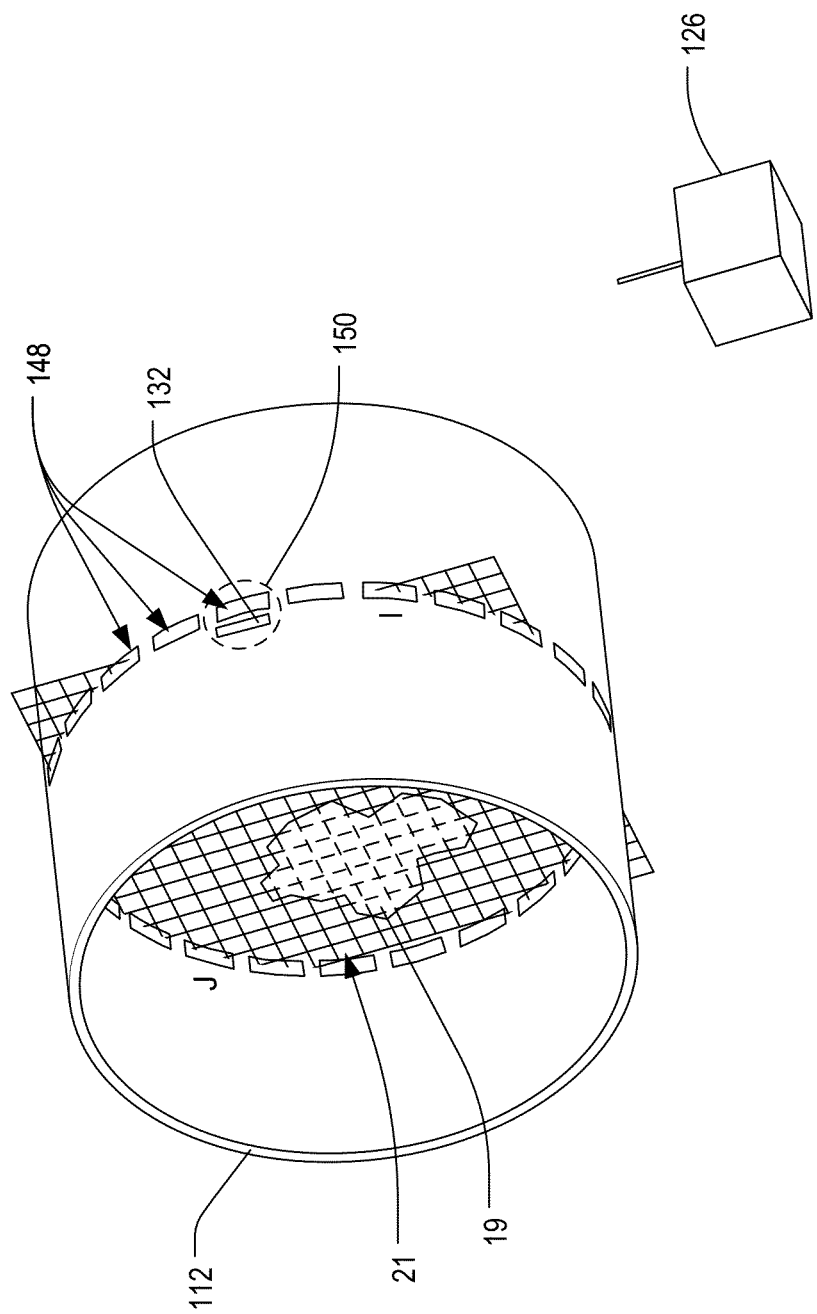
FIG. 6 is a schematic diagram illustrating the operation of the system of FIG. 5 in a two-dimensional context.

FIG. 6 is a schematic diagram illustrating the operation of the boundary apparatus 112 and transmitting/receiving hardware 126 of FIG. 5 in a two-dimensional context. Unlike prior art systems, the transmitting/receiving hardware 126 is not physically connected with the imaging domain 21. In at least some embodiments, the transmitting/receiving hardware 126 is man-portable. As used herein, "man-portable" means capable of being carried or borne by one human. In some embodiments, the transmitting/receiving hardware 126 may be provided in the form of a small cellular base station or "small cell," such as, for example, a femtocell unit. In some embodiments, the transmitter and the receiver are separate devices, while in others the transmitter and receiver are combined in a single unit.

Figure 7:
FIG. 7 is a side perspective view of a cap serving as wearable boundary apparatus in accordance with one or more preferred embodiments of the present invention.

The boundary apparatus 112 is a man-portable hollow structure whose walls are made of material or materials that is or are non-transparent (opaque) with respect to EM waves and thereby defines the boundaries of the imaging domain 21 for the system 110. The boundary apparatus 112 itself may take any of a variety of shapes, forms and the like. In at least some embodiments, the boundary apparatus 112 is in the form of a garment or other wearable object. For example, the apparatus 112 may be a specially-designed shirt, vest, sleeve, bra or other undergarment, cap, or the like. In this regard, FIG. 7 is a side perspective view of a cap serving as wearable boundary apparatus 112 in accordance with one or more preferred embodiments of the present invention.

Regardless of its form, the walls of the boundary apparatus 112 include a pattern of N EM-controlled "transparent" holes or windows 148 (i.e., entry/exit points) distributed so as to surround the imaging domain 21. In some embodiments, the pattern of holes or windows 148 may be a repeating pattern. In other embodiments, the pattern of holes or windows 148 may be a non-repeating pattern. The condition ("open" or "closed") of each entry/exit hole or window 148 may be controlled by a microchip device 132. In at least some embodiments, the open or closed condition of each entry/exit hole or window 148 is individually coded. The combination of the entry/exit holes or windows 148 with their microchip devices 132 are sometimes referred to herein as "EMWindows" 150. In operation, the boundary apparatus 112 is placed around the object under study 19, or the object 19 is placed within the boundary apparatus 112, and the system 110 is activated. During operation of the system 10, the transmitter of the transmitting/receiving hardware 126 is used to generate an EM field that passes through one or more of the entry points 148 and into the imaging domain 21. After interacting with the object 19 of interest, each "interferenced" or scattered EM interrogation field ($E_{sct}$) passes through one or more of the exit points 148, where it is then received at the transmitting/receiving hardware 126. By determining the radiation component corresponding to the traversal from each entry point (hole_i, where 0<i≤N) to each exit point (hole_j, where 0<j≤N) and incorporating location information about the respective entry and exit points 148, as described below, an accurate image of the object 19 within the imaging domain 21 may be determined and reconstructed.

In order to facilitate the use of the interferenced or scattered EM interrogation field ($E_{sct}$) information to properly determine a 2D or 3D spatial distribution of dielectric properties within the object 19, and to thereby reconstruct a 2D or 3D image of the object 19, the microchip devices 132 may be used to control operational aspects of the EMWindows 150. In at least some embodiments, each EMWindow 150 includes a "smart" gate, sometimes referred to as a "microswitch" or "microgate," that may be used by the microchip devices 132 to open or close the entry/exit points. The gates may include the use of PIN diodes. Using these gates, the number of entry and exit holes windows 148 that are open or active at any one time may be varied. In particular, the specific entry and exit holes or windows 148 that are open and closed at any given time may be controlled or determined using control technology, as generally described below, and this information may be coordinated with corresponding measurements of $E_{sct}$.

Figure 8A:
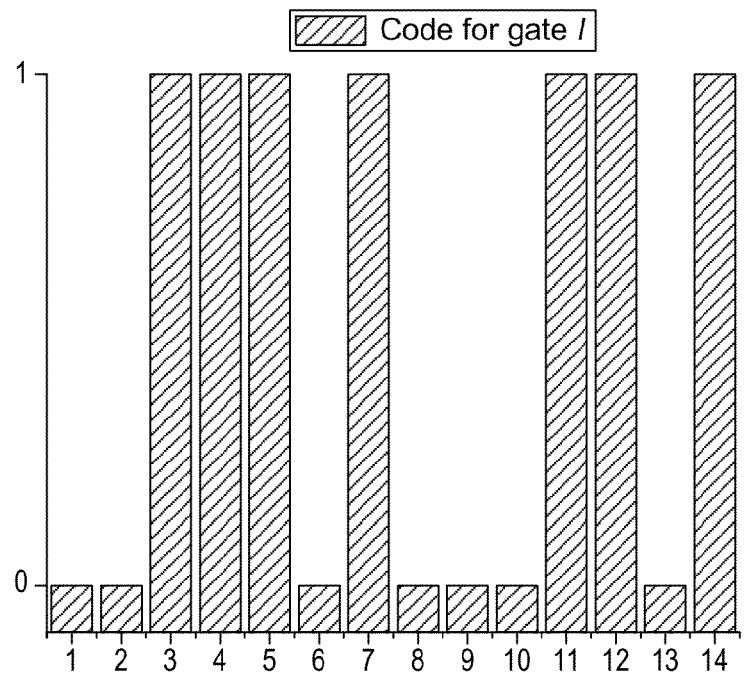
FIGS. 8A and 8B are graphical illustrations of exemplary codes for gates of the boundary apparatus of FIG. 6.
Figure 8B:
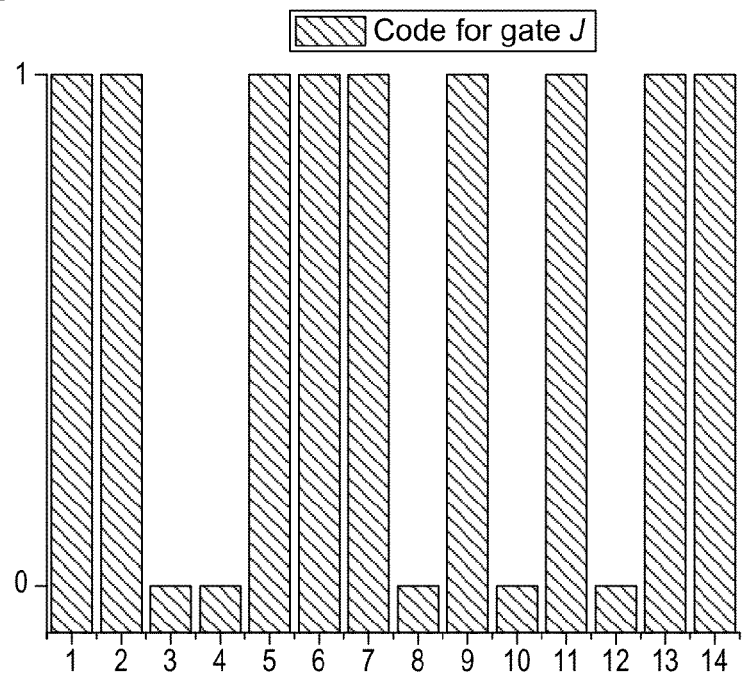
Figure 9A:
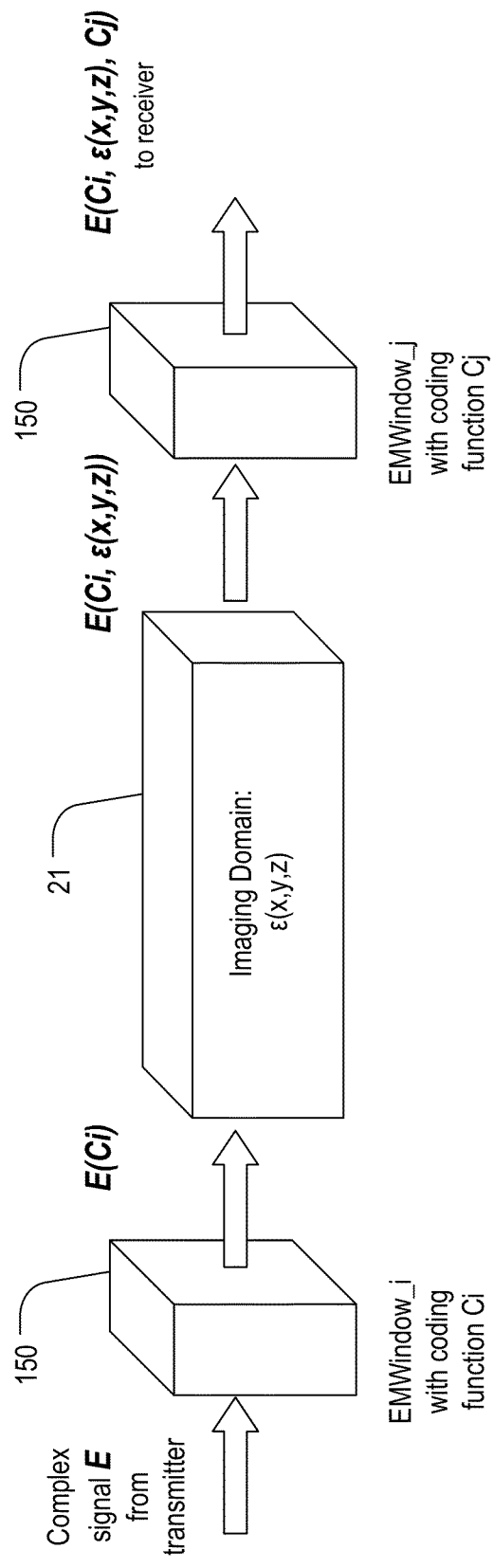
FIG. 9A is a block diagram illustrating use of the EMWindows coding concept.

In at least some of these embodiments, determining the radiation for each unique entry/exit hole pair (i,j) may be achieved by coding the corresponding gates and then applying the coding to the electromagnetic (EM) radiation/waves/field. This may be accomplished, for example, using code-division technology; such technology is described, for example, in the aforementioned U.S. Pat. No. 7,239,731. FIGS. 8A and 8B are graphical illustrations of exemplary codes for gates I and J of the boundary apparatus of FIG. 6, and FIG. 9A is a block diagram illustrating use of the EMWindows coding concept. As shown in FIG. 9A, the transmitter of the transmitting/receiving hardware 126 generates electromagnetic (EM) radiation/waves/field, represented by complex signal E. As the EM waves enter into the imaging domain 21 through one of the NEMWindows (EMWindow_i) 150, the signal E is coded as E(Ci). The coded signal E(Ci) passes through the imaging domain 21, interacting with the tissue at a multitude of spatial points (x,y,z) and thereby acquiring information about the spatial distribution of dielectric properties of the tissue $\in(x,y,z)$ to produce E(Ci, $\in(x,y,z)$). The EM waves then exit the imaging domain 21 through any EMWindow (EMWindow_j) 150 (which could even be the window EMWindow_j through which it entered, although this information may be of little benefit) where the signal is coded again to produce E(Ci, $\in(x,y,z)$, 0). When finally received by the receiving hardware, the EM radiation has thus been coded with the unique signatures of the particular entry/exit pair. Decoding the signatures allows a matrix of complex raw data to be recovered in relation to the particular entry/exit hole pair (i,j). This data is further combined with information regarding the spatial location of i and j (such information being determined, for example, at the EMWindow position block 310 of FIG. 11, described below). Together, this data set (i.e., the complex matrix of raw data combined with spatial locations of "virtual transmitters" or "transmitting windows" (EMWindow_i in this example) and "virtual receivers" or "receiving windows" (EMWindow_j in this example)) is analogous to the data set generated and processed in previous EMT systems (i.e., the complex matrix of raw data combined with spatial locations of actual transmitters and windows). The data set is transmitted to one or more computers in the hub computer system 128 that process the data to produce an image of the object 19 in the imaging domain 21. As with prior art systems, an algorithm called an "inversion" algorithm is utilized in this process.

Figure 9B:
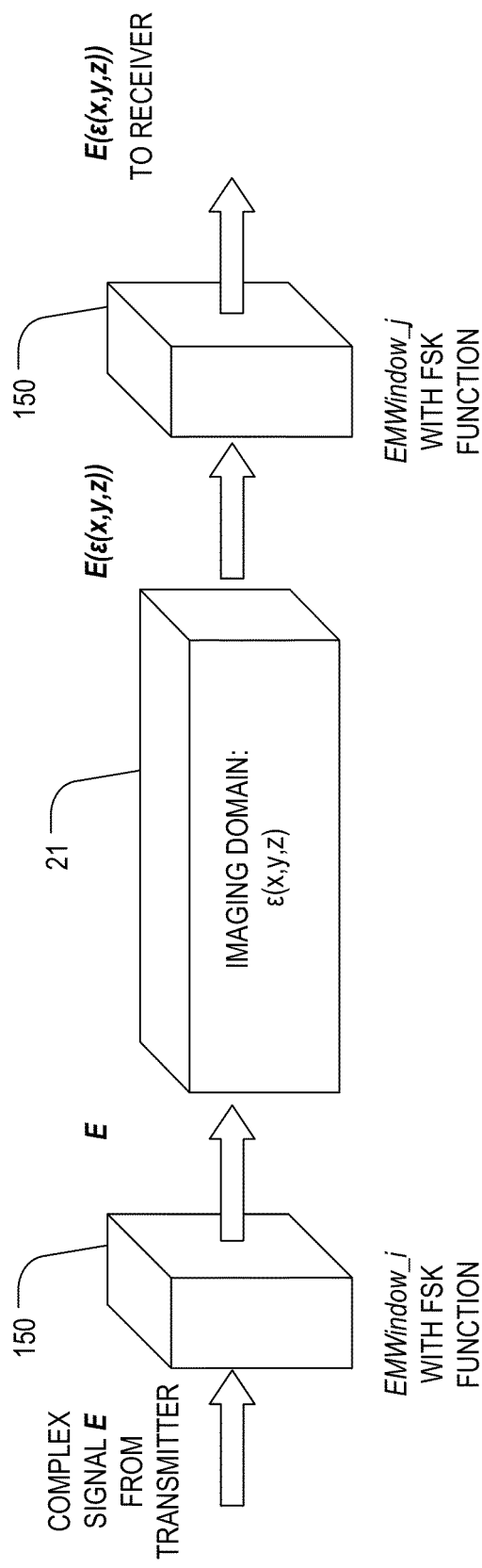
FIG. 9B is a block diagram illustrating use of EMWindows frequency shift keying.

Additionally or alternatively to the use of gate "open/close" coding, in at least some embodiments, determining the radiation for each unique entry/exit hole pair (i,j) may be achieved through the use of frequency shifting using frequency-shift keying (FSK) or the like. FIG. 9B is a block diagram illustrating use of EMWindows frequency shift keying. As shown therein, a frequency shift is applied at each EM entry opening (EMWindow_i), to shift the frequency by some amount $\Delta$Freq_i, and at each EM exit opening (EMWindow_j) to shift the frequency by some amount $\Delta$Freq_j.

In some embodiments, entry and exit holes or windows 148 are opened one at a time, such that only one entry hole or window 148 and one exit hole or window 148 are open during any given measurement. In other embodiments, more than one entry hole or window 148 is open during at least some of the measurements, more than one exit hole or window 148 is open during at least some of the measurements, or both. In some of these embodiments, all of the holes or windows 148 are open during at least some or all of the measurements.

If the specific EMWindows 150 that are open at the time of each $E_{sct}$ measurement are known, and the positions of the open holes or windows 148 at the time of such measurements are known, then the measurements may be used to derive an accurate image of the object 19 within the imaging domain 21. With regard to the positions of the open holes or windows 148, the locations of the holes or windows 148 must either be known ahead of time or must be determinable at the time of measurement. In some embodiments, the boundary apparatus 112 is a generally rigid structure, and the locations of the holes or windows 148 are fixed, relative to each other, by the rigid nature of the boundary apparatus 112. In other embodiments, the boundary apparatus 112 is a flexible structure, and the locations of the holes or windows 148 are not fixed relative to each other and thus must be determined. In either case, because the boundary apparatus 112 is preferably man-portable, and in many embodiments may be frequently moved from place to place, it may be useful to determine the location of the boundary apparatus 112 and to determine the locations of the holes or windows 148 based on their location relative to the boundary apparatus 112. Determining the location of the boundary apparatus 112 and/or the locations of the holes or windows 148 is described in greater detail hereinbelow.

Power Considerations

Consideration must be given to the power requirements of the transmitting/receiving hardware 126. In an exemplary embodiment, the transmitter provides irradiating power on the biological object through the EMWindows 150 in an amount similar to that produced by a conventional mobile phone. Using current technology, a maximal such power level may be between +33 dBm (2 W) and +36 dBm (4 W), which represents the approved power level for maximum output from a GSM850/900 mobile phone (+33 dBm) and for maximum output from a UMTS/3G mobile phone (power class 1 mobile).

Assuming the attenuation at the EMWindows varies from 0 to 20 dB, the attenuation within the biological object (which may be a complete organism, but more likely is merely a part of an organism, such as a human arm or leg) is expected to be within −60 dB to −100 dB. This leads to a power level, after passing through a biological object, of from −24 dBm to −87 dBm. Furthermore, assuming that the signal is attenuated approximately 20 dBm to 30 dBm when it passes from the object to the receiver, the estimated level of the signal on Rx (without any amplification by the boundary apparatus 112) is within a range of −44 dBm to −117 dBm.

By way of comparison, the typical power level of wirelessly-received signals received wirelessly over variants of 802.11 networks, using commercial devices, is within −60 dBm to −80 dBm. The typical received signal power from a GPS satellite is −127 dBm, and the thermal noise floor for 1 Hz bandwidth at room temperature is −174 dBm.

Because the estimated minimal level of the signal is about −117 dBm and the estimated dynamic range for a static position of the object is about 53 dB, the level of the signal and dynamic range are believed to be within performance characteristics of modern telecommunication technologies and may not require any amplification of the signals at the boundary apparatus 112. However, if amplification is desired or preferred, it may be included in or on the microchip device 132. For example, small low-noise amplifiers (LNAs) are readily available commercially. A series of amplifiers suitable for use in preferred embodiments of the present invention is the MAX2686/MAX2688 low-noise amplifier, designed for GPS L1, Galileo, and GLONASS applications and having dimensions 0.86 mm×0.86 mm×0.65 mm, available from Maxim Integrated Products, 120 San Gabriel Drive, Sunnyvale, Calif. 94086.

Frequency Considerations

Signal interference or parasitic cross coupling between EMWindows 150 can occur both inside the boundary apparatus 112 and outside.

Inside the boundary apparatus 112, direct, mutual coupling or interference may occur between EMWindows 150. More particularly, the signal E or E(Ci) entering the imaging domain 21 may, in at least some situations, pass around (rather than through) the body of interest 19 and thus interfere with the signal of interest, i.e., the signal E($\in$(x,y,z)) or E(Ci, $\in$(x,y,z)) that passes through the body of interest 19. In at least some embodiments, this may be addressed using a "matching/decoupling" media (not shown). Such a media may decouple direct, mutual interference caused by a signal signal E or E(Ci) passing around the body of interest 19. One example of such a media is a gel with a high concentration of salt.

Outside the boundary apparatus 112, the signal E being transmitted by the transmitting hardware may, in at least some situations, be powerful and parasitic relative to the signal E($\in$(x,y,z)) or E(Ci,$\in$(x,y,z)) that passes through the imaging domain 21, and thus may interfere with reception thereof by the receiving hardware. Thus, in at least some embodiments, a frequency converter may be utilized at each of the entry EMWindows 150 to create separation between the transmitter frequency and the receiver frequency, thereby avoiding interference with the transmitter signal. For example, a transmitter signal at a frequency of 0.5 GHz may be passed through a frequency doubler to produce an interrogation signal at a frequency of 1.0 GHz. The EM radiation thus passes through the imaging domain 21 at the interrogation frequency and likewise through one or more EMWindows 150 before being received at that frequency as well.

Figure 10:
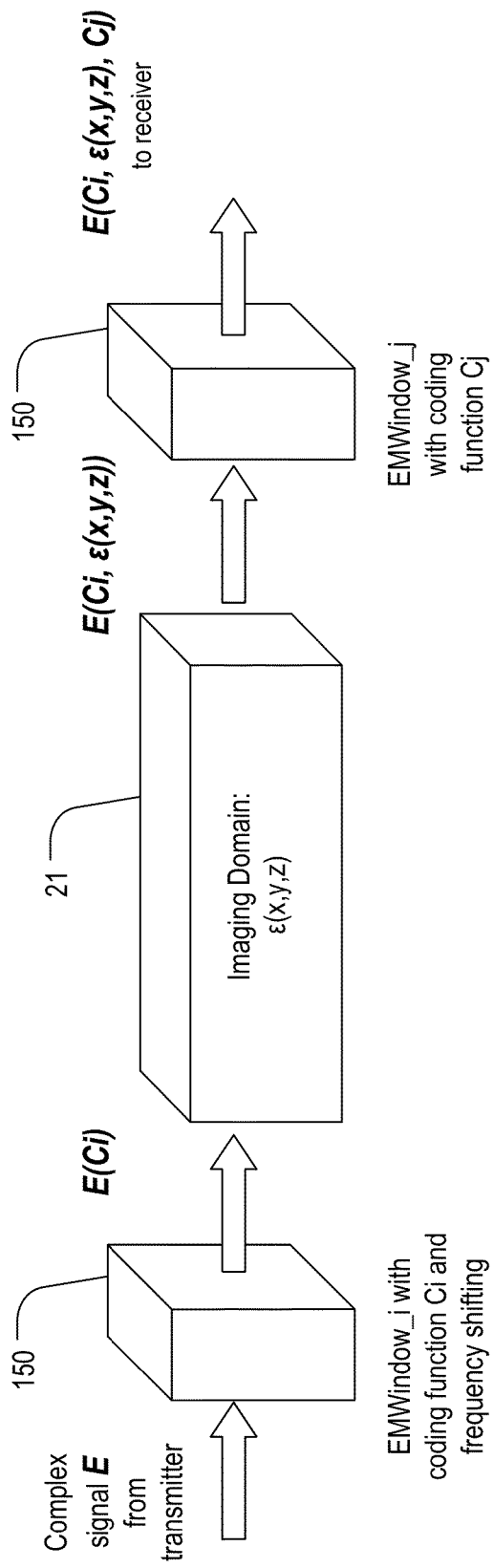
FIG. 10 is a block diagram illustrating use of EMWindows coding together with frequency conversion.

Frequency conversion may be used in conjunction with gate coding described previously. FIG. 10 is a block diagram illustrating use of EMWindows coding together with frequency conversion. As with the EMWindows coding shown in FIG. 9A, the transmitter of the transmitting/receiving hardware 126 generates electromagnetic (EM) radiation/waves/field, represented by complex signal E. The transmission frequency is designated as Freq_Tx. As the EM waves enter into the imaging domain 21 through one of the EMWindows (EMWindow_i) 150, the signal E is coded as E(Ci), and the frequency is shifted by some amount $\Delta$Freq_i. The coded signal E(Ci) passes through the imaging domain 21, interacting with the tissue at a multitude of spatial points (x,y,z) and thereby acquiring information about spatial distribution of dielectric properties of the tissue $\in$(x,y,z) to produce E(Ci, $\in$(x,y,z)), at frequency Freq_Tx+$\Delta$Freq_i. The EM waves then exit the imaging domain 21 through another EMWindow (EMWindow_j) 150, where the signal is coded again to produce E(Ci, $\in$(x,y,z), Cj). When finally received by the receiving hardware, still at frequency Freq_Tx+$\Delta$Freq_i, the EM radiation has thus been coded with the unique signatures of the particular entry/exit pair but has also been shifted in frequency by the amount $\Delta$Freq_i.

In one example, the transmission frequency (Freq_Tx) is 0.5 GHz, and a frequency shift is applied at each EM entry point (EMWindow_i) to shift the imaging frequency (Freq_imaging) upward to 1 GHz. In this regard, it will be appreciated that the frequency may be shifted higher, at least up to 2.5 GHz.

It will also be appreciated that, in accordance with the reciprocity principal:

$$\vec{E}(Ci,\in(x,y,z),Cj)=\vec{E}(Cj,\in(x,y,z),Ci)$$

Therefore, the uniqueness of the coding of each EMWindows pair (Ci,Cj) is independent from the way the EM wave enters the imaging domain 21 assuming the "absolute" similarity of EM and geometrical properties of windows and that plane EM wave is irradiating the object.

The frequency converter may be active or passive. One passive, commercially available frequency doubler suitable for use in the present invention is the miniature Hittite HMC156AC8. Others may likewise be available, and it will be appreciated that the frequency converter may be any suitable frequency multiplier, up-converter, down-converter, or the like.

Other interference issues may exist outside the boundary apparatus 112 as well. In some embodiments, the transmitting hardware may be able to transmit at multiple transmission frequencies. In at least some of these embodiments, a user may select or adjust the transmission frequency so as to avoid interference with other signals that may be present. Similarly, in some embodiments, multiple frequency converters, or frequency converters capable of shifting by a variety of different amounts, may be provided, and in at least some of these embodiments, a user may select or adjust the amount of shift so as to avoid interference.

Boundary Apparatus

In order to determine the data properly and to properly reconstruct an image, it is important to be able to know or determine the position of the boundary apparatus 112 accurately, and ultimately, to be able to know or determine the position of the entry and exit holes or windows 148 accurately. In at least some embodiments, the position of the boundary apparatus 112 within a given operational domain, such as a room, may be determined, and the positions of the entry and exit holes or windows 148 on or in the boundary apparatus 112 are applied thereto in order to determine the position of the entry and exit holes or windows 148 within the operational domain. Additionally or alternatively, the position of the boundary apparatus 112 relative to the transmitting/receiving hardware 126 may be determined, and the positions of the entry and exit holes or windows 148 on or in the boundary apparatus 112 are applied thereto in order to determine the position of the entry and exit holes or windows 148 relative to the transmitting/receiving hardware 126.

The position determination system 180 may be utilized to determine the exact position of the apparatus 112. In this regard, the position determination system 180 may use processes and technology akin to those employed by GPS systems but in a localized setting, with the positional data being directly available, either online or otherwise. The spatial accuracy necessary to produce meaningful results can vary significantly, with significant correlation between the spatial accuracy and the accuracy of the resulting data and image. Table 1 illustrates the required spatial accuracy for the position of the boundary apparatus 112 for several different exemplary transmitting frequencies.

TABLE 1

| Frequency [GHz] | λ air[cm] | 10 deg accuracy [mm] | 1 deg accuracy [mm] |
|---|---|---|---|
| 0.5 | 60 | 17 | 1.7 |
| 1 | 30 | 8 | 0.8 |
| 2.5 | 12 | 3 | 0.3 |

Similarly, data and image accuracy is also affected by the accuracy of information about the shape and dimensions of the EM holes or windows 148. Table 2 illustrates the accuracy for the shape and location of the EM holes or windows 148 relative to the boundary apparatus 112 for different exemplary transmitting frequencies.

TABLE 2

| Frequency [GHz] | λ air[cm] | λ muscle or myocardial tissues[cm] | 10 deg accuracy [mm] | 1 deg accuracy [mm] |
|---|---|---|---|---|
| 1 | 30 | 3.8 | 1 | 0.1 |
| 2.5 | 12 | 1.6 | 0.4 | 0.04 |

The complexity of the problem of accuracy with regard to information about the positions of the entry and exit holes or windows 148 depends, at least in part, on the type of boundary apparatus 112 utilized. For example, the boundary apparatus 112 may be deformable or non-deformable. Examples of non-deformable apparatuses may include a helmet, a sleeve, a bra, a waistcoat, or the like. Notably, non-deformable apparatuses are not necessarily inflexible, but are generally non-elastic. One advantage of non-deformable boundary apparatuses 112 is that the exact 3D location of each EM hole or window 148, relative to the boundary apparatus 112 as a whole, is known ahead of time. However, a non-deformable boundary apparatus 112 may require a larger or thicker "matching/de-coupling" layer.

Examples of deformable boundary apparatuses may include a cap, an "elastic" sleeve, an "elastic" bra, an "elastic" waistcoat, or the like. In contrast to non-deformable apparatuses, deformable boundary apparatuses 112 may advantageously require a smaller or thinner "de-coupling" layer. (Notably, in at least some embodiment, a decoupling layer is utilized even when there is a perfect fit of the boundary apparatus 112 to the biological object of interest, because as stated previously, a significant function of a "de-coupling" media is to decouple direct (around the body 19) mutual interference between EMWindows 150 inside the boundary apparatus 112.) Another advantage is that deformable boundary apparatuses 112 may be worn more comfortably, thereby perhaps better enabling the wearer to work, run, sleep and the like while wearing them. On the other hand, a major disadvantage of deformable boundary apparatuses 112 is that the exact 3D location of each of the EM holes or windows 148, relative to the boundary apparatus 112 as a whole, is not known and has to be located/positioned every time measurements are conducted.

In one approach that may be particularly useful with regard to deformable boundary apparatuses, and may have applicability with non-deformable boundary apparatuses as well, a process of determining EM opening spatial information may be carried out in two stages. First, the exact 3D location for each of the EM holes or windows 148 of the boundary apparatus 112 is determined for a theoretical state wherein the boundary apparatus 112 is in place on or around a "standard" sized object 19. This data is stored in memory in the system 110. Once the boundary apparatus 112 is on a real object 19, the actual locations of the EM holes or windows 148 will vary slightly from the theoretical, "standard" locations, but the theoretical locations may be used as a starting point for subsequent spatial fine-tuning, thereby enhancing and accelerating the process considerably. Spatial fine tuning is preferably within a 3D area of the size of an EM hole or window 148. The position determination system 180 may utilize a localized (e.g., in-room) GPS-type system, a honeycomb algorithm wherein once the position of one cell is determined the position of cells next to it can be determined, or any other suitable system or approach.

Software may be used for fast determination of 3D (x,y,z) position as well as phase-shift correction for the path EMWindow_i-to-receiver and amplitude and phase correction at the entry EMWindows 150 when frequency is changed. In at least some embodiments, it is assumed that amplitude is similar for all EMWindow_i's (i=1 . . . N).

Processing of the Data

The hub computer system 128 (sometimes referred to as the "hub") is the processing center where initial data is pre-processed and images are reconstructed and post-processed. In at least some embodiments, all data processing and imaging software is located in the hub computer system 128 and is controlled by a single entity for commercial, research or other purposes.

Data may be transferred from the transmitting/receiving hardware 126 to the hub computer system 128 in a variety of ways. In various embodiments, the data may be transferred through one or more conventional technologies, including mobile phone communication technology, other wireless communication technology (e.g., Wi-Fi), and/or high speed wired connections.

In at least one embodiment, data is processed directly in the transmitter/receiver hardware 126 or a device communicatively connected directly thereto. If the transmitter/receiver hardware 126 or other device includes a display, it may be possible to prepare and present an image directly on the device without use of a hub computer system. However, the processing resources of such devices may not be sufficient to produce an image quickly or accurately enough to achieve the desired usefulness. Additionally, because central control is not effectuated in such an arrangement, such an arrangement may be disadvantageous from a commercial perspective and/or for other reasons. Thus, if the transmitter/receiver hardware 126 or other device is to be utilized to display an image to a user or to a patient, it may be preferable to send data to the hub control system 128, reconstruct the image at the hub as described below, and then send the image back if needed. The hub 128 provides the desired efficiency, accuracy and control to overcome the foregoing shortcomings.

Image Reconstruction at the Hub Computer System

Figure 11:
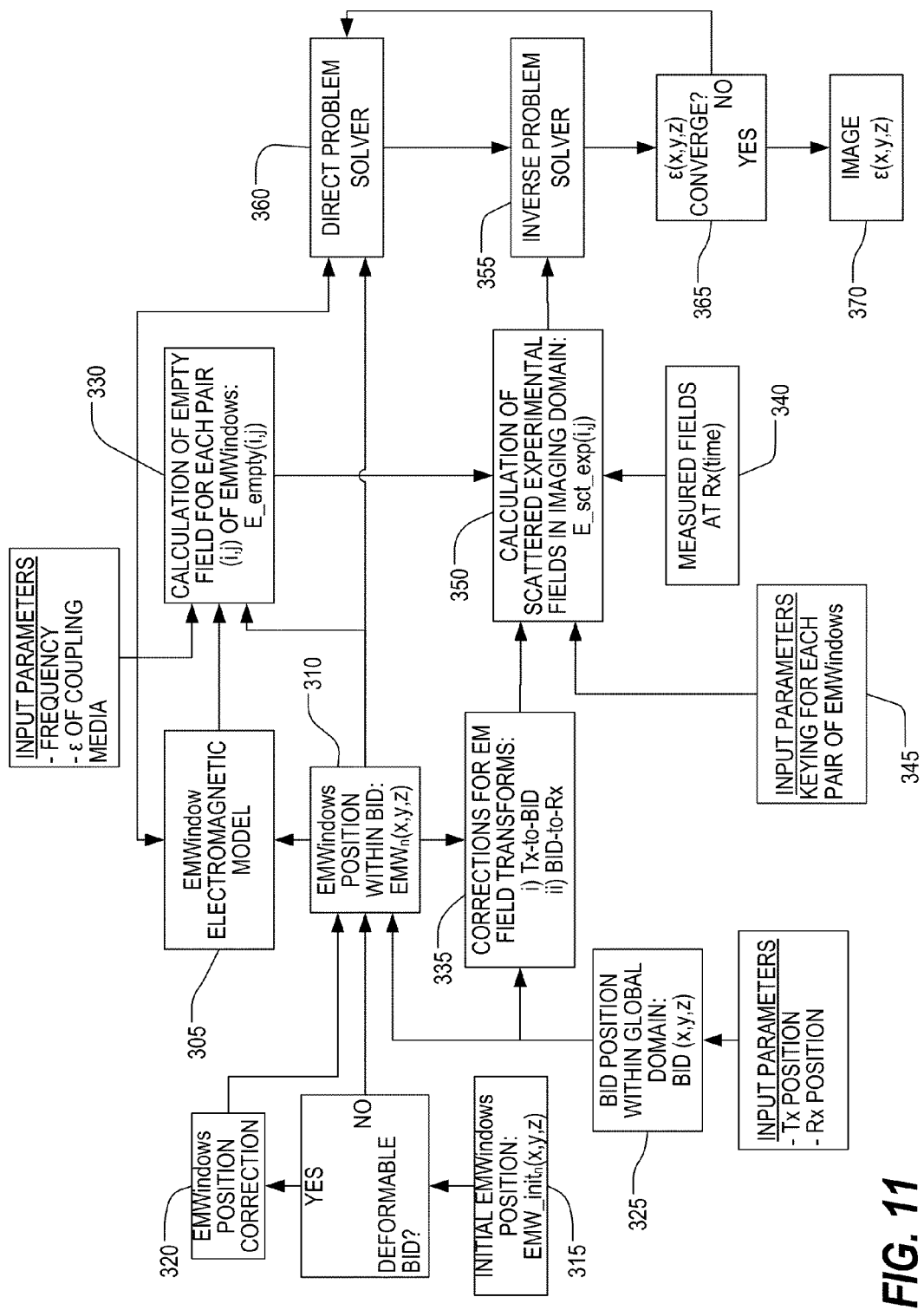
FIG. 11 is a flow diagram illustrating the operation of the hub computer system of FIG. 5.

FIG. 11 is a flow diagram illustrating the operation of the hub computer system 128 of FIG. 5 in accordance with one or more preferred embodiments of the present invention. As shown therein, input parameters, including frequency and permittivity ($\in$) of the coupling media, are provided to an EMWindow electromagnetic model that is developed at block 305. The EMWindow model is further provided with the position of the opening of each EMWindow (n=1 . . . N) ($EMW_n(x,y,z)$) within the boundary apparatus 112, which in FIG. 11 is referred to as the "boundary of imaging domain" ("BID"). This information is developed at block 310. For a non-deformable boundary apparatus, the initial EMWindow positions ($EMW\_init_n(i,x,y,z)$), shown at block 315 may be sufficient, but for a deformable boundary apparatus position correction, shown at block 320, may need to be applied as described above. The EMWindow model also incorporates the position of the boundary apparatus 112 itself ($BID(x,y,z)$) within a global domain as developed at block 325.

The EMWindow position information, the EMWindow electromagnetic model, and the other input parameters are all used in a process at block 330 of calculating an "empty" field $E\_empty(i,j)$ (i.e., the field when the imaging domain 21 is empty) for each particular pair (i,j) of EMWindows (where i and j are each selected from the N total windows). Meanwhile, corrections are developed for EM field transforms at block 335, including transforms for both transmitter-toboundary apparatus (BID) and boundary apparatus-to-receiver, using the relative EMWindow position information and the absolute BID position information developed at blocks 310 and 325.

The flow of raw measured complex EM data into the processing unit is shown at block 340, with keying for each pair of EMWindows occurring at block 345. Calculation of scattered experimental fields in the imaging domain 21 for each pair of EMWindows if (E_sct_exp(i,j)) occurs at block 350 and utilizes the calculated "empty" field data (E_empty(i,j)) from block 330 and corrections from block 335. The calculated data is provided to an iterative inverse problem solver, shown at block 355. The inverse problem solver works in conjunction with a direct problem solver, shown at block 360, that in turn utilizes EMWindow positional information from block 310 to produce a resulting £ for each point (x,y,z). A convergence check is performed at block 365 after each iteration of the inverse problem solver and the direct problem solver is utilized to improve the results until convergence conditions are reached, at which point the results are finalized at block 370 for use in forming an EM image of the object of interest.

Figure 12B:
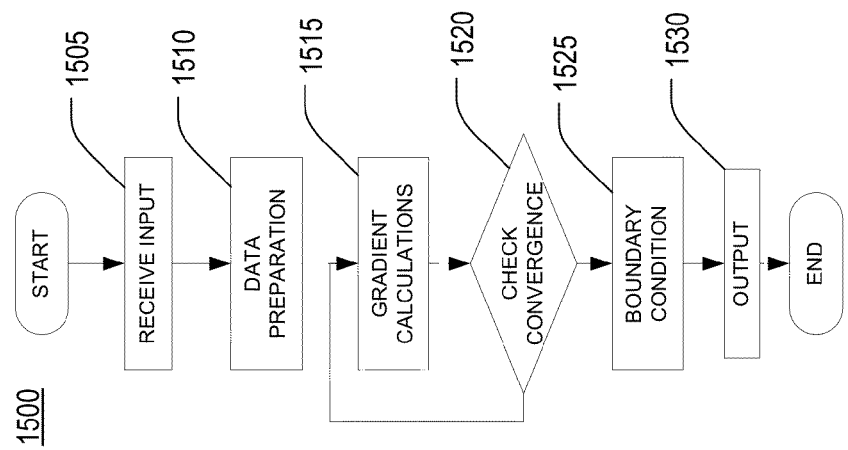
FIG. 12B is a flow diagram of an exemplary inverse problem solver method for optional use in an image reconstruction process.
Figure 12A:
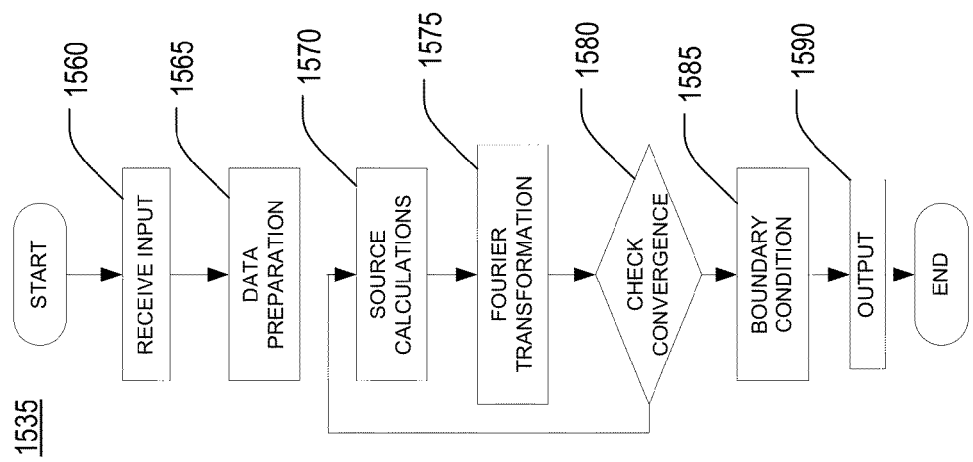
FIG. 12A is a flow diagram of an exemplary direct problem solver method for optional use in an image reconstruction process.
Figure 12C:
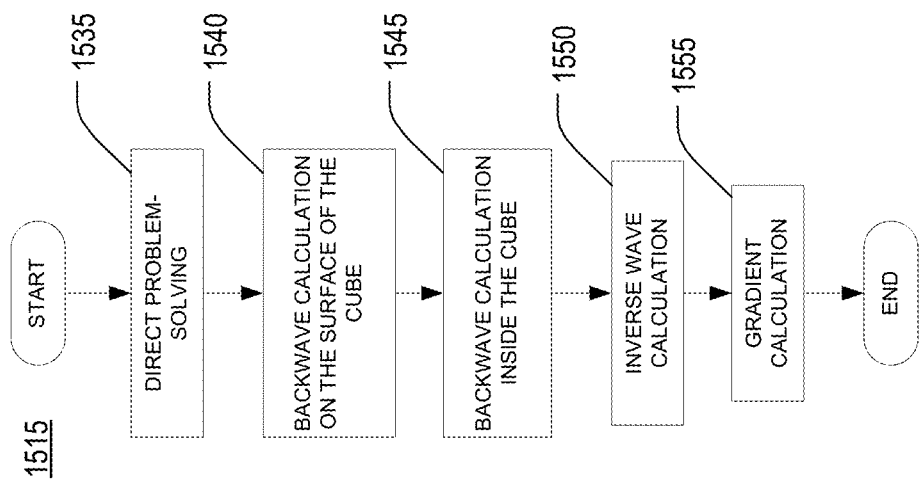
FIG. 12C is a flow diagram of an exemplary gradient calculation method for optional use in an image reconstruction process.

In part, the operation of the hub computer system 128 may rely on a process or processes previously described in U.S. Pat. No. 7,239,731 to solve an inverse problem of electromagnetic field tomography. The solver might be or include, for example, a non-simplified three-dimensional ("3D") vector solver using Maxwell's equations or a simplified 3D scalar solver or a further simplified 2D scalar solver. FIGS. 12A, 12B and 12C are flowcharts of such optional processes. Use is made of an iterative procedure based on either a gradient or a Newton calculation approach or it may use a simplified approach using a Born or Rytov approximation. If a non-approximation approach is used it preferably has one or more of the following features, among others: (i) the method is based on minimization of the difference between model scattered fields and measured scattered fields; (ii) the method uses a regularization method, such as Tikhonov regularization, one of its variants, or the like; (iii) one type of the calculation mesh is used in the method; (iv) one step of the iterative procedure is performed as solving of the two sets of direct problems of the same dimension: modeling of the so-called direct wave and modeling of the inverse wave; (v) both the direct wave and the inverse wave are calculated using nonreflecting or metallic boundary conditions; (vi) both the direct wave and the inverse wave are calculated on the same rectangular mesh; (vii) in order to solve the direct problem a conjugate gradient method ("CGM") might be used; (viii) one step of the CGM uses the sine Fourier transform; (ix) the wave equation for non-uniform media is used to solve the direct problem.

From a mathematical point of view, the methodology utilized in EM field tomography is an inverse problem. It may be formulated in terms of complex dielectric properties ∈ and/or magnetic properties μ and electric and magnetic fields –E, H. The basis is a set of the Maxwell's equations as shown in U.S. Pat. No. 7,239,731 equation (1), where E and H represent electrical and magnetic fields, respectively, and all other notations are standard.

It is more practical to rewrite these equations in a form of non-uniform wave equations such as that shown at U.S. Pat. No. 7,239,731 equation (2), where $$k^2 = (2\pi/\lambda)^2 \in \mu$$

and λ is a wavelength in vacuum. The EM field tomographic system could be schematically represented as a chamber with the set of EM openings on the surface of the chamber. As described previously, the EM holes or windows 148 sometimes function as EM field entry points while at other times functioning as EM field exit points. It is useful to divide electric field E into incident $E_0$ field and scattered field $E_s$, as shown at U.S. Pat. No. 7,239,731 equation (3) where j is the number of a particular entry EM opening or exit EM opening. The equation (2) can be rewritten in the form shown in U.S. Pat. No. 7,239,731 equation (4) where $k_0^2$ is a wave number for homogeneous matter and $E_{0j}$ is the field produced by the EMWindow number j.

An object 19 may be described as a distribution of dielectric permittivity in the imaging domain 21.

The receiver records the signal, which reflects both incident and scattered fields.

In order to solve equation (4) we need to use some boundary conditions on the bound of a calculation domain. Both nonreflecting and reflecting (metallic) boundary conditions may be used on the domain bounds. EMWindows in the current invention play similar roles as transmitting or receiving antennas in classical EM tomographic settings. For this reason: i) the spatial location of EMWindows has to be known (see FIG. 11) and ii) the mathematical model of an EMWindow as an antenna has to be provided. A simple point source or electric or magnetic dipole or Kirchoff type source or final elements model may be used to simulate the function of EMWindows in both transmitting and receiving modes.

Direct Problem Solver

There are various approaches to solving the direct problem. In some embodiments, a conjugate gradient method may be used with a preconditioner. In order to do that, equation (4) may be rewritten in the form shown in U.S. Pat. No. 7,239,731 equation (8), where $k_{av}$ is an average value of k. The preconditioner operator can be constructed as a first step of the iterative process shown at U.S. Pat. No. 7,239,731 equation (9). Taking into account the fact that the left side of equation (8) is an expression with constant coefficient, equation (9) can be solved at step 1575 using sine-type Fourier transform for the case with zero boundary conditions on the bound of calculation domain. Then R. A. James's method (originally invented for static problems, but subsequently developed for electromagnetic problems) is applied to make boundary conditions nonreflected. This technique creates a very robust and effective method. Computational experiments show that the iterative process appears to work with any reasonable contrasts and provides nonreflecting conditions with very high accuracy. Using a sine-type Fourier transform at step 1575 can make calculations 8 times faster than with the regular Fourier approach.

FIG. 12A is a flow diagram of an exemplary direct problem solver method 1535 for optional use in an image reconstruction process. It will be appreciated, however, that other approaches may be used. Furthermore, in at least some embodiments, the direct solver 1535 is used only for inverse problem solving. The input data in this case is the dielectric properties distribution in the form of a 2D or 3D array, which is received at step 1560. For the first step of the iteration, this input data may be received from external input, which in some embodiments may be a homogeneous distribution of dielectric properties of a background (or matching) media, while in other embodiments may be merely an initial "guess" distribution. In subsequent iterations, the input data is received from the previous iteration. Next to occur, at step 1565, is the preparation of the parameters and arrays, which do not change during the direct problem solving process: the wave number, the computational grids, and the Green function for the uniform space. After that, the iterative procedure of the conjugate gradients takes place at steps 1570 1580. First, the source member of equation (4) is calculated at step 1570. Then, every step of the conjugate gradient method requires fast Fourier transforms of the source functions, as shown at step 1575. In order to stop iterations the convergence of the process is checked at step 1580. Once the iterative procedure is finished, the non-reflecting or reflecting boundary conditions have to be implemented at step 1585. Finally, the output of the process 1535 is created at step 1590. The output comprises arrays containing the electric fields inside of the computational domain and signals on the receivers for all transmitter positions.

Inverse Problem Solver

In at least some embodiments, a gradient method may be used to solve the inverse problem in electromagnetic tomography. In the case of a three-dimensional vector in cylindrical geometry this method needs significant modifications when compared with two dimensional and scalar cases. In general the inverse problem in EM field tomography can be formulated as a minimization problem as shown at U.S. Pat. No. 7,239,731 equation (10), where $S_{ij}^{theor}$ are the theoretical values of the signal, $S_{ij}^{exper}$ are experimental values of the signal, and the last term is the Tikhonov regularization functional.

An important point of any minimization procedure is the method of a gradient calculation. It was proven that the gradient of functional in our case is set forth at U.S. Pat. No. 7,239,731 equation (11) where $E_j$ and $G_{ij}$ are solutions of U.S. Pat. No. 7,239,731 equations (12) and (13). Functions $F_j$ and $P_{ij}$ describe the field patterns for EMWindows 150 being used as entry holes or windows 148 and exit holes or windows 148, respectively.

Direct computation using the equation (11) is very time consuming even in the 2D case and cannot be effectively applied in the 3D case. The reason is that every step requires N×M number of direct problems to be solved, where N is the number of transmitters, and M is the number of receivers. In at least some embodiments, the function shown at U.S. Pat. No. 7,239,731 equation (14) can be the solution of U.S. Pat. No. 7,239,731 equation (15). This makes it necessary to solve only two direct problems on each iterative step.

The calculation of the sum in the right side of equation (15) continues to be a difficult problem, because it requires summation on all receivers for all cells of the computational mesh. In order to overcome this obstacle, a two-step procedure may be applied. First, U.S. Pat. No. 7,239,731 equation (16) may be calculated on the surface of the computational domain. This needs significantly less computational effort compared to the calculation of the right part of equation (15). Second, U.S. Pat. No. 7,239,731 equation (17) may be solved with those boundary conditions. Equation (17) is the equation with constant coefficients and can be easily solved using sine-type FFT.

Finally, one step of the gradient method procedure requires solving two direct problems (equations (12) and (15)) plus one equation (equation (17)) with constant coefficients.

One step of the iterative procedure can be implemented as shown at U.S. Pat. No. 7,239,731 equation (18), where an iterative step is chosen in a trial method. The limitations on the upper and lower bounds of the values of the dielectric properties and the values of the dielectric properties on the bound of the object are applied in this step.

FIG. 12B is a flow diagram of an exemplary inverse problem solver method 1500 for optional use in an image reconstruction process. At step 1505, the input data is received. The input data for the inverse problem solver 1500 includes physical and geometrical parameters of the computational process: the sixes of the computational domain, the working frequency, the maximum number of iterations and the signals from the EM holes or windows 148. Next to occur, at step 1510, is the preparation of the parameters and arrays, which do not change during the inverse problem solving iteration process: the wave number, the computational grids, and the Green function for the uniform space. After that, the iterative procedure of calculating the gradient of the residual function (equation (11)) itself takes place at steps 1515, 1520, including the gradient calculation process itself at step 1515. In order to stop iterations the convergence of the process is checked at step 1520. This involves comparing the value of the residual error with the estimated experimental error. Once the iterative procedure is finished, the boundary conditions have to be implemented at step 1525. Finally, the output of the process 1500 is created at step 1530. The output comprises the dielectric properties distribution in the form of a 2D or 3D array.

FIG. 12C is a flow diagram of an exemplary gradient calculation method 1515 for optional use in an image reconstruction process. The direct wave is calculated at step 1535 according to equation (12), followed at step 1540 by the calculation according to equation (16) of the source for back-propagating wave on the bounds of the computational domain. Then, at step 1545, the source of the back-propagating wave is calculated in the volume of the computational domain according to equation (17), and the back-propagating wave is calculated by solving equation (13) at step 1550. Finally, the gradient is calculated according to equation (11) at step 1555.

The image reconstruction algorithm of this invention includes a number of benefits. For example, using the nonreflecting boundary conditions plus sine-type FFT makes the direct problem solver of the invention the most effective one. Further, the proposed way to calculate the so-called back wave (equations (15), (16), (17)) allows working in real 3D multi-point configuration. In addition, the method of signal calculation (equation (7)) is distinguished from any others and allows simulating the work of each EMWindow with high precision, and the mathematical algorithm itself is essentially parallel, which is particularly advantageous for parallel computing.

Application Example

Stroke Diagnosis

Figure 13:
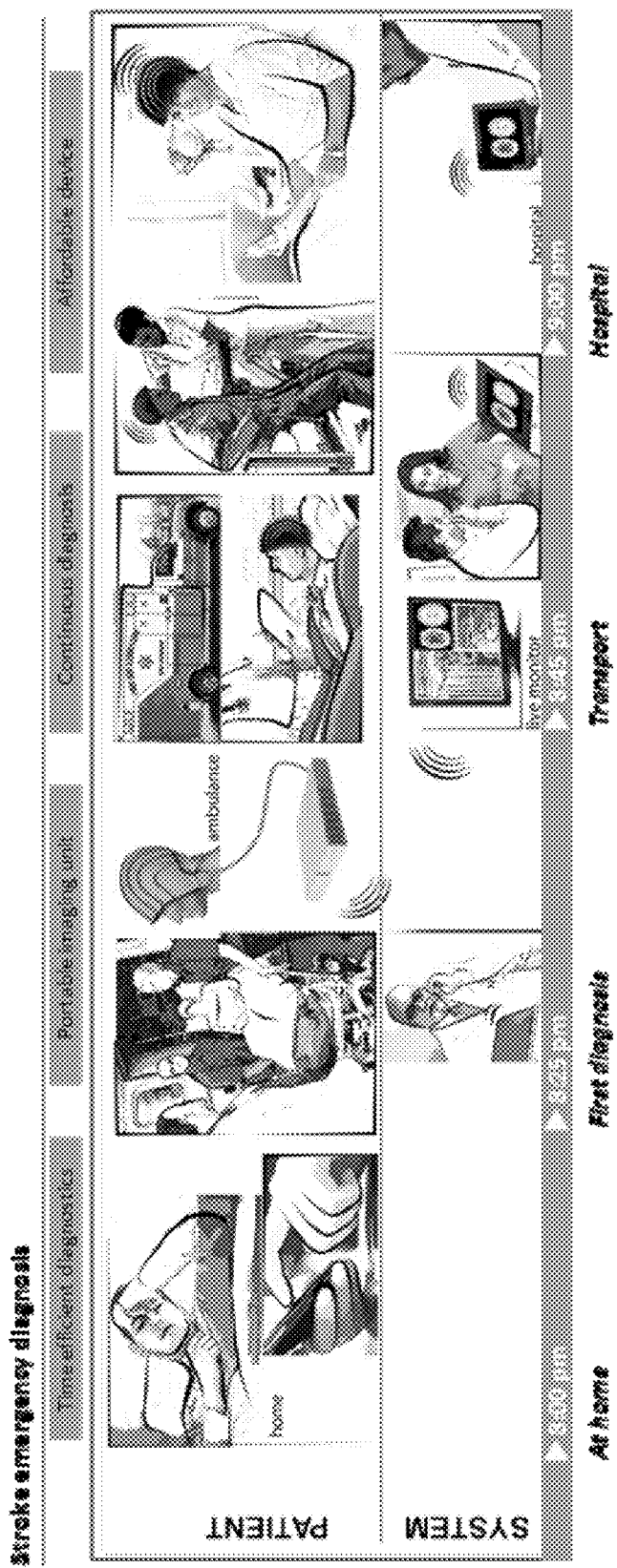
FIG. 13 is a pictorial illustration of a timeline for use of an EMT system, including the cap of FIG. 7, for imaging a human head in response to the onset of stroke symptoms in a patient.

At least some embodiments of the EMT systems presented herein, including without limitation the mobile embodiments such as those presented in FIGS. 12A, 12B and 13, may be utilized advantageously outside of the clinical setting. FIG. 13 is a pictorial illustration of a timeline for use of an EMT system, including the cap 112 of FIG. 7, for imaging a human head in response to the onset of stroke symptoms in a patient. As shown therein, at 8:00 pm, a patient may be resting at home when he experiences the onset of stroke-like symptoms, such as disorientation and weakness in the face and arms. In response, he or a family member or friend contacts a medical provider, and an ambulance is dispatched. Meanwhile, a doctor or other medical practitioner is contacted and updated on the situation. A wearable boundary apparatus 112, such as the cap of FIG. 7, is placed on or around the patient's head, and scanning begins as shown around 8:25 pm. Resulting data may be provided to the doctor, ambulance staff, imaging specialists, and other personnel. Some of the data may be used directly for diagnosis, treatment, or the like, while complex image-related data may be processed according to the systems and methods of the present invention to reconstruct images from which further diagnosis, treatment, or the like may be triggered. In at least some embodiments, such processing may generate an automatic alert that the data indicates that a potential stroke is likely. Notably, in at least some embodiments, such processing is carried out by a third party service provider who specializes in reconstruction of images according to the systems and methods of the present invention. During transport, from approximately 8:45 pm to 9:00 pm, the cap 112 continues to provide data regarding the patient's condition, and the local hospital staff is further updated and arranges and prepares for further treatment. Once the patient arrives at the hospital or other treatment center, the images and data may be used in providing timely, accurate information about the status of the stroke injury, and appropriate treatment and follow-up may be administered. Such a system could be utilized to provide the desired "under 3 hour" treatment that can make a major difference in the final outcome of the stroke injury and its affect on the patient.

Substitution or Other Use in Known EMT Systems

Figure 14:
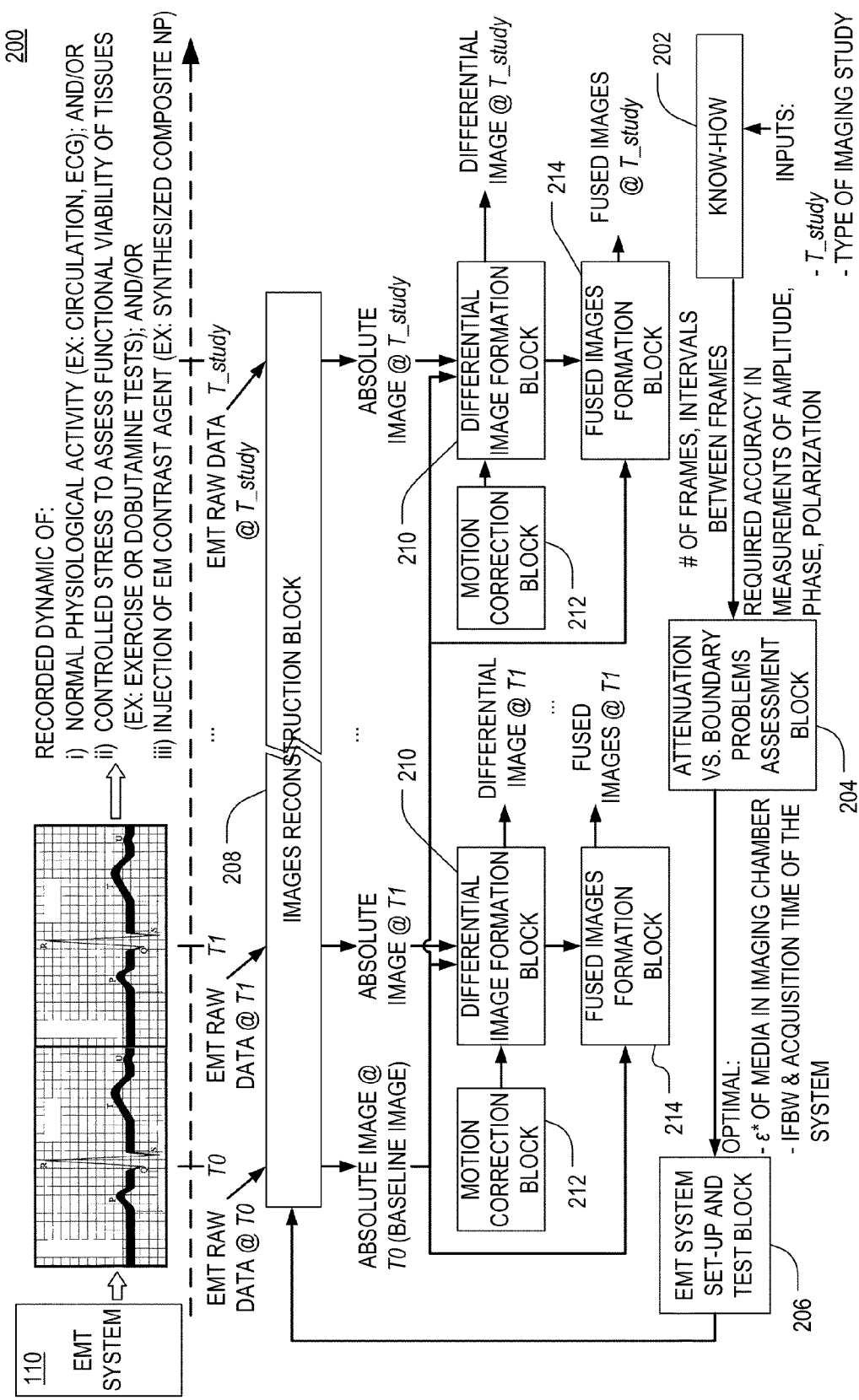
FIG. 14 is a schematic diagram illustrating the use of the system and methods of FIGS. 5-12C in an exemplary 4D EMT differential (dynamic) fused imaging system.

It will be appreciated that various elements of the present invention may be further utilized in various systems that may have heretofore utilized conventional EMT technology. For example, FIG. 14 is a schematic diagram illustrating the use of the system 110 and methods of FIGS. 5-12C in a 4D EMT differential (dynamic) fused imaging system 200. At least in part, the operation of such a system 200 may be carried out using components, and according to a process or processes, previously described in U.S. Patent Application Publication No. 2012/0010493 A1. As used herein, $\in^*$ means a complex number, unless otherwise indicated. The system includes a "know-how block" 202, an "attenuation vs. boundary problems assessment block" 204, "an EMT system set-up and test block" 206, an "images reconstruction block" 208, a "differential image formation block" 210, a "motion correction block" 212, and a "fused images formation block" 214.

As shown in the lower right-hand corner, two important inputs into the method and system are the type of imaging study and the time duration of the study (T_study). The type of imaging study may, for example, be i) a dynamic study of normal physiological activity within soft tissue of extremity or myocardial tissue or brain tissue, ii) a controlled stress study to assess a functional viability of tissues (for example myocardium or muscle tissue) during physical stress (exercise) or pharmacologically induced stress (for example using dobutamine as per already approved clinical procedure), iii) an injection of electromagnetic contrast agent(s) (e.g., synthesized composite functional nanoparticles), or the like, or a combination of the foregoing. The time duration of the study (T_study) may be input, for example, in units of seconds or a number of cycles of physiological activity (for example, cardiac cycles).

Based on the input, the system calculates, as represented by the "know-how" block 202, various desired system parameters. These preferably include the required timely resolution (timely intervals between each EMT acquisition cycle (frame)), the number of frames to be acquired by the system, the required accuracy of measurements in amplitude, the required accuracy of measurements in phase, and the required accuracy of measurements in polarization (if needed).

Using this information, the "attenuation vs. boundary problems assessment block" 204 may calculate i) optimal dielectric properties ($\in^*_0 = \in'_0 + j\in''_0$) of matching media (to be filled around the object 19 in the boundary apparatus 112), mainly by optimizing an attenuation component ($\in''_0$), and ii) IFBW of the system based on required timely resolution and number of channels of the system to be acquired. Then a matching/decoupling media is prepared by mixing water, alcohol, salt, glycerol and/or other components at an appropriate concentration to match desired dielectric properties ($\in^*_0 = \in'_0 + j\in''_0$). The boundary apparatus 112 may then be fully or partially filled (for making "empty" measurements or for making actual "in use" measurements, respectively) with such media, which in at least some embodiments is in gel-type form. In particular, as represented by the "EMT system set-up and test block" 206, the system 200, including the EMT system 110, is first set up and initialized and, with the boundary apparatus 112 fully filled with matching media, a test is conducted on this "empty" boundary apparatus—i.e., with the boundary apparatus 112 filled with matching/decoupling media but with no object 19 inside. This allows for assurance that the desired system parameters are met. Then, when the system 200 is ready, the object 19 under study is placed into the boundary apparatus 112, along with the matching/decoupling media. In at least some embodiments, the matching media is spread on the inner surfaces of the apparatus 112 before placing the object 19 into the apparatus 112.

With the object and the matching/decoupling media in place, and full set EMT data (frames) are acquired as described above at each time T0, T1 . . . T_study. The raw EMT data at each time frame comes into an image reconstruction block 208 to calculate an absolute anatomical image at each time frame T0, T1 . . . T_study. The absolute anatomical image that is determined at time T0, which may sometimes be referred to herein as a "BaseLine image," is used to calculate a differential image and fused images at all further frames T1 . . . T_study. For frame T0, the starting point (initial distribution of dielectric properties within an imaging domain) for an iterative image reconstruction procedure may be a homogeneous distribution of matching media $\in^*_0 = \in'_0 + j\in''_0$ within an imaging domain. For all other frames (T1 . . . T_study), the starting point may be a homogeneous distribution of matching media $\in^*_0 = \in'_0 + j\in''_0$ within an imaging domain (a BaseLine image ($\in^*_{frame\ T0}$)), or alternatively, the starting point may be a reconstructed image from previous frame. In other words, a BaseLine image ($\in^*_{frame\ T0}$), which is a reconstructed distribution of dielectric properties at time T0, can be used as a starting point for image reconstruction at other time points (frames) T1 . . . T_study, or alternatively an image reconstructed at time Tt ($\in^*_{frame\ Tt}$) can be used as a starting point for image reconstruction at frames t+1, t+2 etc. This significantly accelerates an image reconstruction procedure by decreasing a required number of iterations.

The "differential image formation block" 210 calculates differential images between the initial frame T0 and the current frame Tt as follows:

$$\in^*_{diff} = (\in^*_{frame\ Tt} - \in^*_{frame\ T0})/\in^*_{frame\ T0} \times 100\ [\%]$$

It is strongly preferred that the reconstructed images at time T0 and Tt are to be motion free. In spite of a very short acquisition time (preferably on the order of a dozen milliseconds or less), motion correction might be required. This may be conducted in the "motion correction block" 212.

A fused image at each time frame Tt may be obtained via the "fused images formation block" 214. In one exemplary implementation, a background image, representing the absolute anatomical image of the biological object 19, is produced using a gray palette, and a time-differential image, produced using a color palette, is superimposed over the background image. In this example, bony areas having low dielectric properties may be rendered in the absolute anatomical image using darker shades of gray while soft tissue areas may be rendered in the absolute anatomical image using lighter shades of gray. Also in this example, the degree of changes may be rendered in the time-differential image, which reflects physiological activity or interventions during the study, along a color spectrum such that each particular color represents a percentile of change. Simple examples of such fused images, obtained during preliminary experiments using the foregoing systems and methods described above, are provided in the aforementioned U.S. Patent Application Publication No. 2012/0010493 A1.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A method of electromagnetic tomographically imaging a live human body part using a wearable boundary apparatus, comprising:
    installing a wearable and portable boundary apparatus such that the apparatus is worn around a body part by a live human while the human moves from one place to another, the wearable and portable boundary apparatus being a hollow structure whose walls include a plurality of electromagnetic windows;
    determining position information pertaining to the wearable boundary apparatus with respect to an external frame of reference;
    generating an electromagnetic field, externally with reference to the wearable boundary apparatus, that passes into and out of the wearable boundary apparatus through the electromagnetic windows;
    independently opening or closing the electromagnetic windows to control whether the electromagnetic field passes therethrough, wherein the step of independently opening or closing the electromagnetic windows is carried out via a respective microgate for each electromagnetic window;
    receiving the electromagnetic field after being scattered/interferenced by the live human body part; and
    generating electromagnetic tomographic images based upon the generated and received electromagnetic field, upon the determined position information, and incorporating information about a spatial location of each of the plurality of electromagnetic windows.

2. The method of claim 1, wherein the walls of the hollow structure define the boundaries of an imaging domain and are made at least partly of a material that is non-transparent with respect to the generated electromagnetic field, and wherein the plurality of electromagnetic windows are distributed in the walls so as to surround the imaging domain.

3. The method of claim 1, wherein the step of independently opening or closing the electromagnetic windows includes controlling the microgates such that the electromagnetic field passes into the boundary apparatus through only one electromagnetic window at a time.

4. The method of claim 1, wherein the step of independently opening or closing the electromagnetic windows includes controlling the microgates such that the electromagnetic field passes into the boundary apparatus through a plurality of electromagnetic windows at a time.

5. The method of claim 1, wherein the step of independently opening or closing the electromagnetic windows includes controlling the microgates such that the electromagnetic field passes out of the boundary apparatus through only one electromagnetic window at a time.

6. The method of claim 1, wherein the step of independently opening or closing the electromagnetic windows includes controlling the microgates such that the electromagnetic field passes out of the boundary apparatus through a plurality of electromagnetic windows at a time.

7. The method of claim 1, wherein each microgate is individually coded.

8. The method of claim 7, further comprising a step, as the electromagnetic field enters the boundary apparatus through an open electromagnetic window, of applying the coding of the microgate for the open electromagnetic window to the electromagnetic field.

9. The method of claim 1, wherein the step of determining position information pertaining to the wearable boundary apparatus is carried out by a position determination system, and the method further comprises a step of determining, via the position determination system, the information incorporated about the spatial location of each of the plurality of electromagnetic windows.

10. The method of claim 1, wherein the step of determining position information pertaining to the wearable boundary apparatus is carried out by a position determination system, and the method further comprises a step of establishing, independently of the position determination system, the information incorporated about the spatial location of each of the plurality of electromagnetic windows.

11. The method of claim 1, further comprising a step of determining, via the position determination system, information about the position of the boundary apparatus, and wherein the step of performing electromagnetic tomographic imaging is performed by a hub computer system based upon the received electromagnetic field and upon the boundary apparatus position information from the position determination system.

12. The method of claim 1, further comprising a step of determining, via the position determination system, information about the positions of the electromagnetic windows, and wherein the step of performing electromagnetic tomographic imaging is performed by a hub computer system based upon the received electromagnetic field and upon the electromagnetic windows position information from the position determination system.

13. The method of claim 1, wherein the step of determining position information pertaining to the wearable boundary apparatus includes determining information, via a first position determination system, about the position of the boundary apparatus, wherein the step of determining position information pertaining to the wearable boundary apparatus further includes determining information, via a second position determination system, about the positions of the electromagnetic windows, and wherein the step of performing electromagnetic tomographic imaging is performed by a hub computer system based upon the received electromagnetic field and upon the boundary apparatus position information and electromagnetic windows position information from the position determination system.

14. The method of claim 1, wherein the boundary apparatus is in the form of a wearable hat, and wherein the step of installing a wearable and portable boundary apparatus includes wearing the hat on the head of the live human.

15. The method of claim 1, wherein the boundary apparatus is in the form of a wearable shirt, and wherein the step of installing a wearable and portable boundary apparatus includes wearing the shirt on the torso of the live human.

16. The method of claim 1, wherein the boundary apparatus is in the form of a wearable vest, and wherein the step of installing a wearable and portable boundary apparatus includes wearing the vest on the torso of the live human.

17. The method of claim 1, wherein the boundary apparatus is in the form of a wearable sleeve, and wherein the step of installing a wearable and portable boundary apparatus includes wearing the shirt on an arm of the live human.

18. The method of claim 1, wherein the boundary apparatus is in the form of a wearable undergarment.

19. The method of claim 18, wherein the wearable undergarment is a wearable bra, and wherein the step of installing a wearable and portable boundary apparatus includes wearing the bra around the breasts of the live human.

20. The method of claim 1, wherein the steps of generating and receiving the electromagnetic field are carried out by electromagnetic transmitting/receiving hardware, and wherein the electromagnetic transmitting/receiving hardware is man-portable.

21. The method of claim 1, wherein the steps of generating and receiving the electromagnetic field are carried out by electromagnetic transmitting/receiving hardware, and wherein the electromagnetic transmitting/receiving hardware is a small cellular base station.

22. The method of claim 1, wherein the steps of generating and receiving the electromagnetic field are carried out by electromagnetic transmitting/receiving hardware, and wherein the electromagnetic transmitting/receiving hardware includes transmitting hardware that is man-portable.

23. The method of claim 1, wherein the steps of generating and receiving the electromagnetic field are carried out by electromagnetic transmitting/receiving hardware, and wherein the electromagnetic transmitting/receiving hardware includes receiving hardware that is man-portable.

24. The method of claim 1, wherein the steps of generating and receiving the electromagnetic field are carried out by electromagnetic transmitting/receiving hardware, and wherein the electromagnetic transmitting/receiving hardware is physically separate from the boundary apparatus.

25. The method of claim 1, wherein the step of generating electromagnetic tomographic images is carried out by a hub computer system.

26. A method of electromagnetic tomographically imaging a live human body part using a wearable boundary apparatus, comprising:
    on a live human, installing a wearable boundary apparatus whose walls include a plurality of electromagnetic windows;
    determining position information pertaining to the wearable boundary apparatus with respect to an external frame of reference;
    via a respective microgate for each electromagnetic window, independently opening or closing an electromagnetic windows to control whether the electromagnetic field passes therethrough;
    generating the electromagnetic field, externally with reference to the wearable boundary apparatus, that passes into and out of the wearable boundary apparatus through one or more of the open electromagnetic windows;
    receiving the electromagnetic field after being scattered/interferenced by the live human body part; and
    generating electromagnetic tomographic images based upon the generated and received electromagnetic field, the determined position information, and spatial location information for each of the open electromagnetic windows.

27. The method of claim 26, wherein the spatial location information for each of the open electromagnetic windows is previously known.

28. The method of claim 26, further comprising a step of determining the spatial location information for each of the open electromagnetic windows.

29. The method of claim 26, wherein the spatial location information for each open electromagnetic window pertains to a location of the window relative to the wearable boundary apparatus.

30. The method of claim 26, wherein the spatial location information for each open electromagnetic window pertains to a location of the window relative to an external frame of reference.

* * * * *